US010234325B2

(12) United States Patent
Tobia et al.

(10) Patent No.: US 10,234,325 B2
(45) Date of Patent: Mar. 19, 2019

(54) INTEGRATED, EXTENDABLE ANESTHESIA SYSTEM

(71) Applicant: Spacelabs Healthcare LLC, Snoqualmie, WA (US)

(72) Inventors: Ronald Tobia, Sun Prairie, WI (US); Andrew Levi, Madison, WI (US); Lee Dalgety, Middleton, WI (US); Cory Boudreau, Madison, WI (US); Gary Choncholas, Madison, WI (US); Bruce Dammann, Middleton, WI (US)

(73) Assignee: Spacelabs Healthcare LLC, Snoqualmie, WA (US)

( * ) Notice: Subject to any disclaimer, the term of this patent is extended or adjusted under 35 U.S.C. 154(b) by 645 days.

(21) Appl. No.: 14/739,270

(22) Filed: Jun. 15, 2015

(65) Prior Publication Data
US 2017/0165440 A1 Jun. 15, 2017

Related U.S. Application Data

(63) Continuation of application No. 12/906,081, filed on Oct. 16, 2010, now Pat. No. 9,086,313.
(Continued)

(51) Int. Cl.
*A61M 16/01* (2006.01)
*A61B 50/10* (2016.01)
(Continued)

(52) U.S. Cl.
CPC .............. *G01F 23/64* (2013.01); *A61B 50/10* (2016.02); *A61G 12/001* (2013.01); *A61M 16/0051* (2013.01); *A61M 16/01* (2013.01); *A61M 16/024* (2017.08); *G01F 1/22* (2013.01); *A61M 16/022* (2017.08); *A61M 16/101* (2014.02); *A61M 16/22* (2013.01); *A61M 2205/584* (2013.01); *A61M 2205/587* (2013.01); *A61M 2209/084* (2013.01)

(58) Field of Classification Search
CPC .. A61M 16/00; A61M 16/0051; A61M 16/01; A61M 16/104; A61M 16/18; A61M 16/20; A61M 16/22; A61M 2016/1035; A61M 2205/583; A61M 2205/584; A61M 2205/587; A61M 2039/1044; A61M 2209/082; A61M 2209/084; A61M 2209/086; A61G 12/001; A61B 50/10; A61B 50/13
See application file for complete search history.

(56) References Cited

U.S. PATENT DOCUMENTS

| 4,148,312 A | * | 4/1979 | Bird | A61M 16/00 128/202.13 |
| 4,323,064 A | * | 4/1982 | Hoenig | A61M 16/00 128/202.22 |
| 4,991,576 A | * | 2/1991 | Henkin | A61M 16/00 128/202.27 |

(Continued)

*Primary Examiner* — (Jackie) Tan-Uyen T Ho
*Assistant Examiner* — Joseph D Boecker
(74) *Attorney, Agent, or Firm* — Novel IP

(57) ABSTRACT

The specification describes anesthesia systems with an integrated, extendable clinical center and clinician/anesthesia office that accommodates for physical separation of clinical and clerical functions. The disclosed anesthesia systems allow for a portion of the system to be brought closer to the patient such that clinical controls can be accessed while tending to the patient airway, without compromising office space available to the clinician or crowding the patient area.

20 Claims, 32 Drawing Sheets

Related U.S. Application Data

(60) Provisional application No. 61/252,269, filed on Oct. 16, 2009.

(51) Int. Cl.
    *A61G 12/00*     (2006.01)
    *A61M 16/00*     (2006.01)
    *G01F 23/64*     (2006.01)
    *G01F 1/22*     (2006.01)
    *A61M 16/22*     (2006.01)
    *A61M 16/10*     (2006.01)

(56) References Cited

U.S. PATENT DOCUMENTS

| | | | | |
|---|---|---|---|---|
| 5,537,992 | A * | 7/1996 | Bjoernstijerna | A61M 16/186 128/200.19 |
| 5,692,494 | A * | 12/1997 | Pernetti | A61M 16/00 128/200.24 |
| 9,086,313 | B2 * | 7/2015 | Tobia | G01F 23/64 |
| 9,844,637 | B2 * | 12/2017 | Beduhn | A61M 16/0051 |
| 2002/0040954 | A1 * | 4/2002 | Roberts | B60R 11/02 248/121 |
| 2006/0053034 | A1 * | 3/2006 | Hlathein | G06Q 10/06 705/2 |
| 2006/0290525 | A1 * | 12/2006 | Andersen | A61M 16/0051 340/632 |
| 2009/0206713 | A1 * | 8/2009 | Vilkas | A61B 50/10 312/209 |
| 2011/0146676 | A1 * | 6/2011 | Dallam | A61B 90/35 128/203.12 |
| 2012/0180789 | A1 * | 7/2012 | Tobia | A61M 16/0051 128/203.12 |
| 2012/0186583 | A1 * | 7/2012 | Drapes | F16M 11/08 128/203.12 |

* cited by examiner

INTEGRATED, EXTENDABLE ANESTHESIA SYSTEM

CROSS-REFERENCE TO RELATED APPLICATIONS

The present application relies on U.S. Provisional Patent Application No. 61/252,269, entitled "Integrated Anesthesia System", and filed on Oct. 16, 2009, and is hereby incorporated by reference in its entirety.

FIELD OF THE INVENTION

The present invention relates to medical systems. More particularly, the present invention relates to an anesthesia system, having an integrated, extendable clinical center and clinician/anesthesia office.

BACKGROUND OF THE INVENTION

Anesthesiologists spend many hours in relatively straightforward cases requiring their vigilance, but little direct clinical action. They are often required to perform various paperwork and documentation activities with only an anesthesia system's tabletop as a work surface. Further, there are typically no storage areas for their documents, files, and personal items, such as cell phones, keys, computers, glasses, wallets, purses, etc. Still further, the clinical usage area of a conventional anesthesia system provides no convenient location for syringes, laryngoscopes and other clinical equipment. Conventional designs of anesthesia systems do not accommodate separation of clinical and clerical functions. Most systems provide only modest amounts of space for the anesthesiologist to conduct their work and that must be shared with space used for clinical setup of drugs and instruments.

Further, most current anesthesia system designs provide no articulation of the breathing circuit connections in order to provide a closer pneumatic and sensor link to a patient. Since most current breathing system designs are completely integrated into the anesthesia system, the entire system must be brought in close proximity to the patient in order to have access to the necessary clinical controls while attending to the patient and their airway. This physical architecture drives the need for very small footprint systems, which further limit the space available for the anesthesiologist to work on.

While some conventional prior art anesthesia systems allow for the breathing circuit to be articulated away from the system and be placed in close proximity to the patient, these systems still have most of their clinical controls located on the main body of the system, thus making use quite cumbersome.

For example, a typical, conventional anesthesia system employs a breathing circuit on a double-hinged tubular arm that can be moved away from the anesthesia system trolley. This requires draping of the hoses from the breathing system to the trolley, including fresh gas hoses, ventilator drive gas and scavenging gas—all with the possibility of leakage and disconnection. Further, the ventilation, FGF and vaporizer controls on this system are located back on the trolley and away from the user's direct clinical interaction with the patient. This is disadvantageous in that the user constantly needs to turn away from the patient to observe monitoring or make adjustments. Also, the tubular arm is prone to damage by excessive applied forces from beds, people etc. when in the extended position.

Some newer conventional anesthesia systems have fixed the breathing circuit and the controls on the trolley frame, requiring the user to bring the entire system closer to the patient. This has forced a reduction in system size, thereby reducing the "workspace" available to the anesthesiologists. In addition, the anesthesiologist's work area for documentation and storage is also brought proximate to the patient and the clinical field which is undesirable from a clinical and space management standpoint. In the alternative, a user can position the system further away from the patient, but then must constantly turn back and forth from the patient to observe the monitoring and make setting changes.

Hence, currently available anesthesia systems do not provide the necessary storage area, types, or connectivity required by a modern day anesthesiologist. These include power attachments and storage for personal electronic products such as computers, PDAs, data/mobile phone devices, personal music devices, wireless headsets etc. Considering that many anesthesiologists do not have offices within the hospitals in which they work, there is a need to satisfy the user of the anesthesia system with enhanced provisions for conducting their daily activities, including case documentation. Some of the features required such as tape dispensers, lined garbage bins and documentation storage areas, etc., are commonly found in office environments, but nevertheless have not been integrated onto currently available anesthesia systems.

What is therefore needed is an anesthesia system which accommodates separation of clinical and clerical functions. What is also needed is an anesthesia system that allows for a portion of the system to be brought closer to the patient such that clinical controls can be accessed while tending to the patient airway, without compromising office space available to the clinician or crowding the patient area.

In addition, conventional anesthesia systems are equipped with alarms designed to alert a user to potential technical problems occurring with the system's behavior. These alarms are typically short text strings that fit within a limited space for display on a video screen provided on the anesthesia system and thus cannot provide detailed information describing the technical issue causing the alarm. Also, these alarm strings may be required to be translated into various localized languages that may not reflect the error as unambiguously as the designers may have envisioned in the English language. Some prior art product designs include posting of additional descriptive text or graphic representations on the video screen describing the potential problem being reflected by the alarm. However, these require more focused attention of the clinical user to read or try to correlate the graphic to the actual system that they are using. Oftentimes, the alarms for anesthesia systems occur during a medical emergency situation, creating a confusing and tense situation for the user. In addition, many users are not familiar with the intricate details of the system's function and cannot easily correlate an alarm message to the necessary corrective actions. Further, many users utilize various manufacturer's systems that may use identical or similar alarm messages to define differing equipment failures, problems or behaviors. Also, the shortened text strings and/or translations used for alarm messages do not present sufficient information to allow the user to adequately diagnose the problem. Hence, an improved alarm display system is required.

Some conventional anesthesia machines are currently fitted with "Alarm Silence" buttons that can be pressed to silence the audible portion of the system's alarms for periods of up to two minutes. This function ensures that the alarm is specifically acknowledged and directly silenced by the user. However, requiring that the alarm silence button be physically pressed can be frustrating to users who have their hands occupied with the care of the patient (e.g. suctioning, re-intubating, administering drugs). Consequently, what is needed is a method for silencing the alarms in a non-contact, yet still reliable manner. This is especially true when the user is being barraged by a series of alarms all related to a single event or clinical condition. For example, alarms that sound during suction of a patient, low pressure alarms, leakage alarms, low Minute Volume alarms, and low Tidal Volume alarms may all be activated at different times.

Further, most conventional anesthesia systems have a function referred to as "$O_2$ Flush". The flush is used principally for refilling the bellows in the presence or upon correction of a leak and for flushing anesthetic agent out of a circle system. Upon activation of the $O_2$ flush for the purposes of refilling the bellows, the bellows fills up with gas that does not contain anesthetic agent. Consequently, the anesthesiologist is required to rebalance the amount of anesthetic agent present in the circuit in order to ensure correct treatment of the patient. Hence, it is desirable to have a single action function in order to provide a high flow similar to that of the $O_2$ flush, while employing levels of mixed gas and anesthetic agent that have been user predefined, in order to enable the bellows to be refilled while preserving the previously set gas mixtures and anesthetic agent levels.

Precise monitoring of the volumes and pressures delivered to ventilated patients is extremely important, especially when presented with pulmonary complications. Measuring these flows and pressures at the patient's airway provides substantial advantages as compared to measuring these parameters inside the anesthesia machine. Current proximal sensors utilize pneumatic or electrical connections back to the Anesthesia system. This connection creates significant bulk and weight at the patient's airway that can lead to disconnections and physical pulling on the patient's endotracheal tube. Consequently, many users perceive this to be a significant disadvantage of proximal sensors and choose to perform patient monitoring and delivery control at a less desirable location closer to the anesthesia system. Further, the use of differential pressure type flow sensors and proximal airway pressure sensors require the use of pneumatic tubes to be attached to the anesthesia system. These tubes can be kinked or occluded by wheels of equipment being moved in the OR, causing data loss on the sensor channel. Pneumatic tubes can also be a source of gas leakage from the breathing circuit and their length can result in flow measurement errors due to pneumatic signal transit, common mode errors. Hence, a single, small sensor solution for proximal placement without tubes or connections back to the anesthesia system is therefore needed.

Contemporary anesthetic vaporizer systems contain valves and/or wick systems for transitioning liquid anesthetic agent into a gaseous form. Typically, these systems provide an agent concentration level of 0-10% (although sometimes higher for Suprane) of the gas being used as "fresh gas" or "make up" gas in a circle breathing system. Contemporary devices are rather complex and require precision mechanical components or flow control systems to operate, creating a relatively high cost device. U.S. Pat. No. 6,155,255 (the '255 patent), herein incorporated by reference in its entirety, proposes a method for generation and control of anesthetic vapor in a flow stream. The '255 patent describes injection of liquid agent into a porous "evaporator" media, through which breathable gas is flowing. However, the '255 patent is disadvantageous in that it does not adequately describe additional elements that would be necessary in order to utilize the patent in a practical manner. In particular, it is desirable to know the amount of gas flow being moved through the evaporator and have direct means for determining the concentration of anesthetic in the breathable gases that is being produced. It is also desirable to precisely measure the amount of liquid flow into the evaporator for the purposes of computing agent concentrations, etc. Hence, means of incorporating a known vaporizer system into an anesthesia system are required.

SUMMARY OF THE INVENTION

In one embodiment, the present invention is an anesthesia system, having an integrated, extendable clinical center and clinician/anesthesia office that accommodates for physical separation of clinical and clerical functions. In another embodiment, the present invention is an anesthesia system that allows for a portion of the system to be brought closer to the patient such that clinical controls can be accessed while tending to the patient airway, without compromising office space available to the clinician or crowding the patient area.

In one embodiment, the present invention is an anesthesia delivery system, comprising a first section comprising support for at least one clinical control and at least one patient connection for providing therapy to a patient, wherein said at least one patient connection includes a breathing circuit connection, comprising at least one limb, wherein the at least one limb may be inspiratory, expiratory or a combination thereof and a second section, comprising a base portion for supporting and housing the first section and further comprising supports for pneumatic and electrical connections and wherein the first section is extendable relative to the second section, exposing at least one workspace when extended, and wherein the second section is pneumatically connected to the first section via a suction supply and at least one anesthesia gas supply.

In one embodiment, the first section of the present invention further comprises a clinical center section which includes at least one of: a ventilator display; a physiological monitor; a physiologic monitor display; respiratory gas analysis and connections; Patient Suction Controls; Auxiliary Oxygen Controls and Connections; Fresh Gas Flow Mixing and Controls; Vaporizers and Attachment Back Bar; Syringe Pump Mounts; Expandable Clinical Workspace; and Wireless Sensor Docking.

In one embodiment, the second section of the present invention further comprises an anesthesia office section which includes at least one of: space for an anesthesiologist's documentation, storage and personal effects; work surfaces to support both the standing and sitting behavior of the anesthesiologist; pull-out trays that allow for a computer keyboard; personal electrical equipment connectors on the front of the anesthesia office section; foot rest with angled front to allow knee room; and lighting of work areas for operation in low light conditions.

In one embodiment of the present invention, the second section further comprises a base portion which includes a sliding track upon which first section is rotatably extendable from a fully integrated position into a first extended position relative to the second section.

In one embodiment, the first section is rotatably extendable from the second section at an angle ranging from 0 degrees to 45 degrees and optionally, rotatably extendable in angular increments.

In another embodiment of the anesthesia delivery system of the present invention, the first section is linearly extendable from the second section, in a range of 0 to 14.5 inches, into a second extended position relative to the second section.

In yet another embodiment of the anesthesia delivery system of the present invention, the first section is, from a fully integrated position, both rotatably and linearly extended away from the second section such that it is in a third and fully extended position. In one embodiment, the anesthesia delivery system of the present invention further comprises at least one floor contact point providing load-bearing support. In one embodiment, the at least one floor contact point is a rotating trackball. In another embodiment, the at least one floor contact point is a rotating caster wheel having multiple rollers for both inline and side to side movement. In yet another embodiment, the at least one floor contact point is configured with appropriate geometry to move obstructions on the floor as the first section is extended away from the second section. In one embodiment, of the anesthesia delivery system of the present invention, a user-initiated actuation results in a motorized movement of the first section relative to the second section. In another embodiment, the motorized movement of the first section is automatically stopped if an obstruction to the movement is detected. In one embodiment, the obstruction is detected by detecting a change in electric current drawn by a movement motor contained within the system. In yet another embodiment, an audio, visual, or audio-visual alarm is provided if an obstruction to the movement is detected.

In an optional embodiment of the anesthesia delivery system of the present invention, the patient is connected to the system via a circle-less breathing circuit which comprises an inspiratory and an expiratory valve, wherein fresh gas is injected through the inspiratory valve, mixed with an injected agent, delivered to a patient and then led out via the expiratory valve and wherein the inspiratory valve further comprises a plurality of control valves to blend at least two of oxygen, air and nitrous oxide directly into the breathing circuit.

In one embodiment, the anesthesia system of the present invention further comprises an information projection lighting system for indicating the status of a control of the system by directly illuminating the controlled function.

In one embodiment, the present invention is an anesthesia delivery system, comprising: a first section comprising support for at least one clinical control and at least one patient connection for providing therapy to a patient, wherein said at least one patient connection includes a breathing circuit connection, comprising at least one limb, wherein the at least one limb may be inspiratory, expiratory or a combination thereof; a second section, comprising a base portion for supporting and housing the first section and further comprising supports for pneumatic and electrical connections, wherein the first section is linearly and rotatably extendable relative to the second section, and wherein the second section is pneumatically connected to the first section via a suction supply and at least one anesthesia gas supply; and an information projection lighting system for indicating the status of at least one function of the system by direct illumination.

In one embodiment, the information projection lighting system further comprises adjustable lighting, wherein the lighting can be adjusted by color, intensity or flash rate.

In another embodiment, the information projection lighting system of the present invention indicates an anomalous operational condition of the anesthesia system by direct illumination of the portion of the anesthesia delivery apparatus suspected of causing the anomalous operating condition.

In another embodiment, the information projection lighting system indicates when a ventilator within the anesthesia system is in an active state by illuminating a bellows of the ventilator.

In yet another embodiment, the information projection lighting system indicates when a ventilator within the anesthesia system is in an inactive state by illuminating an APL valve of the ventilator.

In yet another embodiment, the information projection lighting system indicates when a ventilator within the anesthesia system is in an inactive state by illuminating a pressure gauge of the ventilator.

In yet another embodiment, the information projection lighting system indicates when a ventilator within the anesthesia system is in an inactive state by illuminating a bag arm of the ventilator.

In yet another embodiment, the information projection lighting system illuminates a Common Gas Outlet Port of the anesthesia system when controls are set to have gas emerge from the Common Gas Outlet Port.

In yet another embodiment, the information projection lighting system illuminates an auxiliary flow tube if auxiliary flow has been turned on.

In yet another embodiment, the information projection lighting system illuminates a $CO_2$ absorbent canister if the canister is disengaged from the breathing circuit and/or if there is an alarm for high $CO_2$ in the respiratory gas.

In yet another embodiment, the information projection lighting system illuminates a side stream respiratory gas monitor water trap if the respiratory gas monitor is alarming to indicate an obstruction.

In another embodiment, the present invention is directed toward an anesthesia delivery system, comprising a first section comprising housing for at least one clinical control and at least one patient connection for providing therapy to a patient, wherein said at least one patient connection includes a breathing circuit connection, comprising at least one limb, wherein the at least one limb may be inspiratory or expiratory or a combination thereof; and a second section, comprising a base portion for supporting the first section, a planar workspace surface, at least one pneumatic connection and at least one electrical connection, wherein the second section is pneumatically connected to the first section by a suction supply line and at least one anesthesia gas supply line and wherein the first section is movable relative to the second section. The planar workspace surface should be of sufficient length and width (or depth) to enable an anesthesiologist to comfortably take notes, such a space can be, but is not limited to 3 in×3 in, 8.5 in ×11 in, 11 in×14 in or any dimensional increment therein (3 inches to 11 inches or 3 inches to 14 inches).

Optionally, the second section comprises an area for housing at least one of: a storage space, a first work surface at first elevation, a second work surface at a second elevation, wherein the first elevation is higher than the second elevation; at least one pull-out tray; at least one electrical equipment connector wherein said connector interface extends outward toward the front of said second section; an angled planar surface at said base of the second section adapted to function as a foot rest; and lighting. The first work surface at a first elevation is preferably a planar workspace surface of sufficient length and width (or depth) to enable an anesthesiologist to comfortably take notes, such a space can be, but is not limited to 3 in×3 in, 8.5 in ×11 in, 11 in×14 in or any dimensional increment therein (3 inches to 11 inches or 3 inches to 14 inches), which is of a sufficient elevation to allow an average size person to stand and write on surface. The first elevation can be two feet or higher. The second work surface at a second elevation is preferably a planar workspace surface of sufficient length and width (or depth) to enable an anesthesiologist to comfortably take notes, such a space can be, but is not limited to 3 in×3 in, 8.5 in ×11 in, 11 in×14 in or any dimensional increment therein (3 inches to 11 inches or 3 inches to 14 inches), which is of a sufficient elevation to allow an average size person to sit and write on surface. The first elevation can be three feet or lower.

Optionally, the base portion of the second section comprises a sliding track upon which first section is rotatably extendable from a first position to a second position. In the first position, the second section and the first section are integrated into each other. It should be appreciated that the second and first section may integrate or be otherwise pulled into each other by having the second section embed itself into the first section, the first section embed itself into the second section, having the external housings of both the first and section sections meet to thereby prevent any access into the internal workspace areas of the second section, or otherwise close. In the second position, the first section extends away from said second section and provides physical access to the planar workspace surface.

Optionally, the first section is rotatably extendable from the second section at an angle ranging from 0 degrees to 45 degrees. The first section is rotatably extendable in angular increments. The first section is configured to linearly extend from the second section in order to move from a first position to a second position, as described above. The first section is linearly extendable from the second section at a distance ranging from 0 to 14.5 inches.

Optionally, the first section is, from a fully integrated position, both rotatably and linearly extended away from the second section such that it is in an extended position. Optionally, the delivery system comprises at least one floor contact point providing load-bearing support. Optionally, the at least one floor contact point is a rotating trackball. Optionally, the at least one floor contact point is a rotating caster wheel having multiple rollers for both inline and side to side movement. Optionally, a user-initiated actuation results in a motorized movement of the first section relative to the second section. Optionally, the motorized movement of the first section is automatically stopped if an obstruction to the movement is detected by a controller, wherein said controller is configured to detect a change in electric current drawn by a movement motor causing said motorized movement. Optionally, an audio, visual, or audio-visual alarm is provided if an obstruction to the movement is detected. Optionally, the patient is connected to the system via a circle-less breathing circuit which comprises an inspiratory and an expiratory valve, wherein fresh gas is injected through the inspiratory valve, mixed with an injected agent, delivered to a patient and then led out via the expiratory valve and wherein the inspiratory valve further comprises a plurality of control valves to blend at least two of oxygen, air, or nitrous oxide directly into the breathing circuit. Optionally, the system further comprises a lighting system for indicating the status of a control of the system by directly illuminating the controlled function. In one embodiment, the lighting system only illuminates a control who status has changed, is in an alert condition, or which otherwise requires the attention of the physician while not illuminating any other control.

Optionally, the second section and first section are only in physical communication with each other at the point of the structures responsible for enabling the rotating or linear movement. Optionally, the second section and first section are not physically connected at any other point except where the second section supports the first section for the purpose of enabling the rotating or linear movement.

In another embodiment, the anesthesia delivery system comprises a first section comprising support for at least one clinical control and at least one patient connection for providing therapy to a patient, wherein said at least one patient connection includes a breathing circuit connection, comprising at least one limb, wherein the at least one limb may be inspiratory, expiratory or a combination thereof; a second section, comprising a base portion for supporting and housing the first section and at least one pneumatic or electrical connection, wherein the first section is linearly, rotatably or linearly and rotatably extendable relative to the second section, and wherein the second section is pneumatically connected to the first section via a suction supply line or an anesthesia gas supply line; and a lighting system for indicating the status of at least one function of the system by direct illumination.

The aforementioned and other embodiments of the present shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings, wherein.

DETAILED DESCRIPTION OF THE INVENTION

The present invention is directed towards an anesthesia system, having an integrated, extendable clinical center and clinician/anesthesia office. The present invention is directed towards an anesthesia system which accommodates for physical separation of clinical and clerical functions. The present invention is also directed towards an anesthesia system that allows for a portion of the system to be brought closer to the patient such that clinical controls can be accessed while tending to the patient airway, without compromising office space available to the clinician or crowding the patient area.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1A:
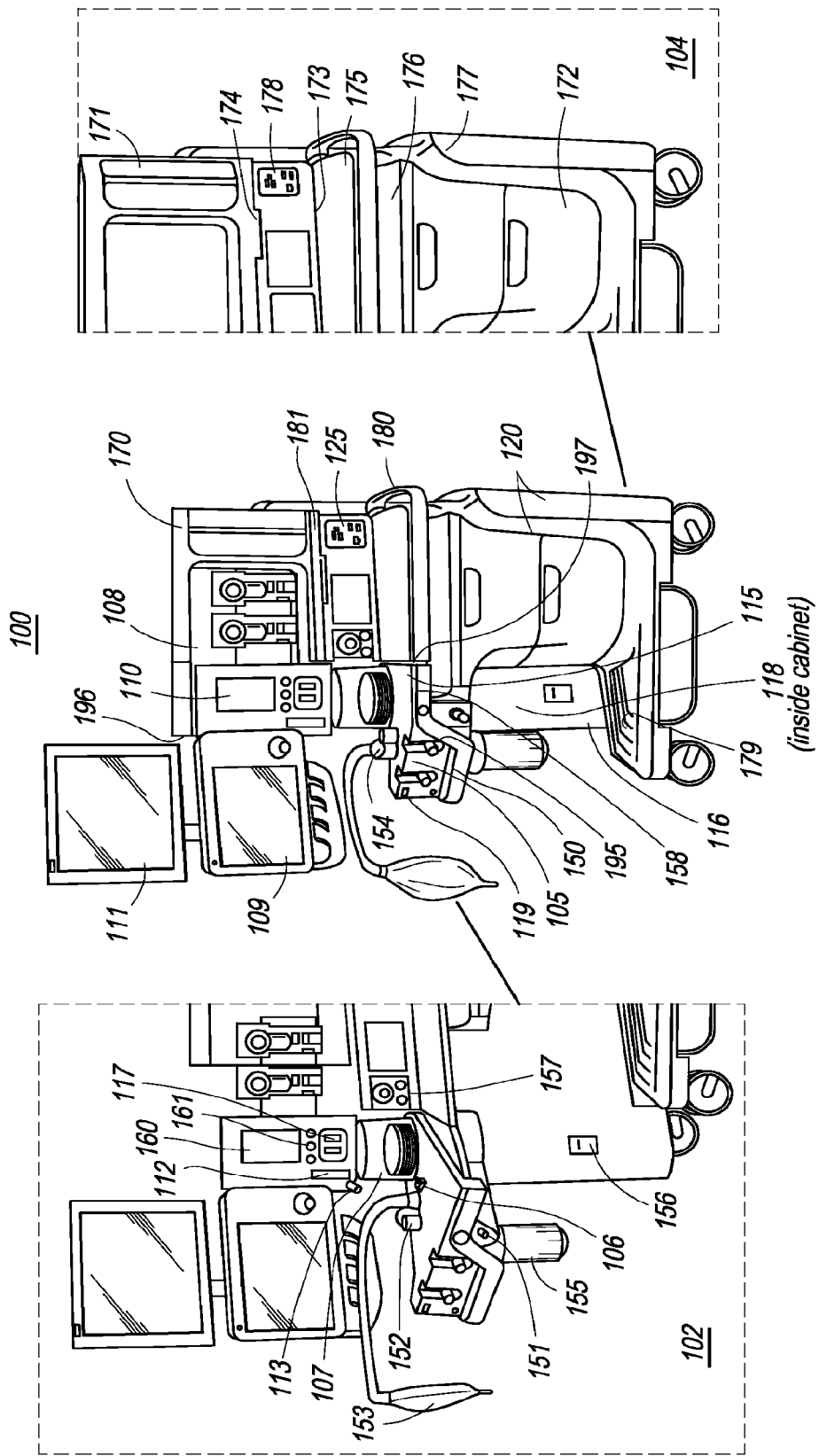
FIG. 1A is an overview illustration of the anesthesia system of the present invention, with cut-away diagrams of the Clinical Center and the Anesthesia Office sections.
Figure 1B:
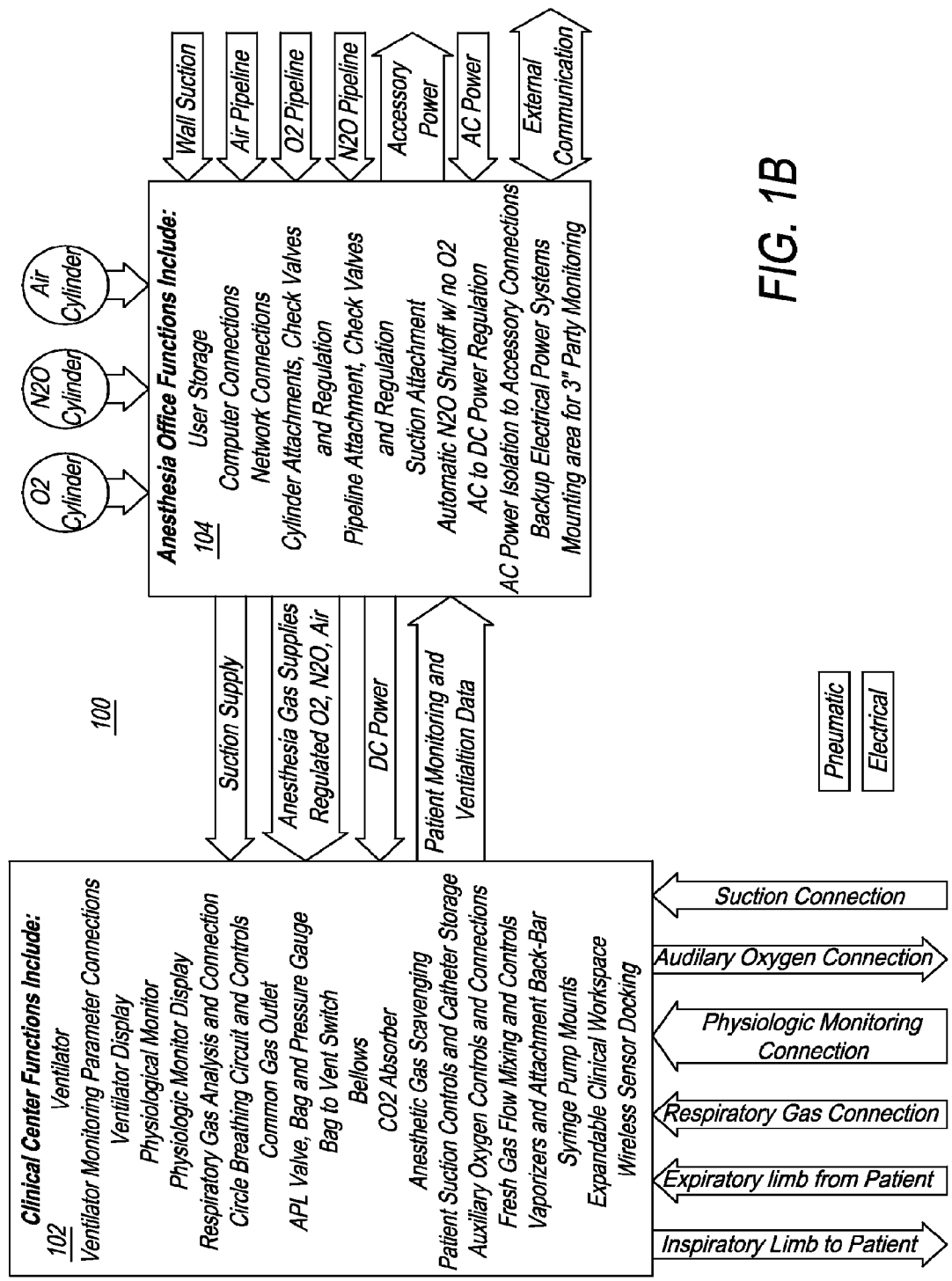
FIG. 1B is a system flow diagram of the anesthesia system of the present invention.

FIG. 1A and FIG. 1B illustrates one embodiment of the anesthesia system 100 of the present invention, which allows for proper workflow management of the anesthesiologist's work area. The anesthesia system 100 of the present invention is a small, compact system configuration, and can be easily moved in close proximity to a patient's bedside. In one embodiment, the present invention provides an anesthesia system that comprises a first section 102 and a second section 104, where the first section 102 includes support for at least one clinical control and at least one patient connection for providing therapy to a patient. In one embodiment, the patient connection includes a breathing circuit. In one embodiment, the second section 104 comprises a base portion for supporting and receiving the first section 102. In addition, the second section 104 comprises pneumatic and electrical connections. In one embodiment, the second section 104 is pneumatically connected to the first section 102 via a suction supply and at least one anesthesia gas supply. In one embodiment, first section 102 is extendable relative to the second section 104 and is capable of moving on a sliding track out from the base provided on the second section 104. In one embodiment, the track is positioned at an oblique angle, to the front face and base of the second section, allowing the movement of the first section to move forward and left from the second section.

In one embodiment, the first section 102 comprises a Clinical Center (CC) section and the second section 104 comprises an Anesthesia Office (AO) section.

Clinical Center (CC) and Clinician/Anesthesia Office (AO)

In one embodiment, "Clinical Center" (CC) section 102 of the anesthesia system 100 illustrated in FIG. 1A comprises at least one clinical control and at least one patient connection for providing therapy to a patient.

As shown in the upper level system architecture of FIG. 1B, the anesthesia system 100 comprises both pneumatic and electrical connections. Referring now to FIG. 1B, the clinical center (CC) 102 is, in operation, pneumatically connected to the patient via at least one breathing circuit connection. In one embodiment, the breathing circuit comprises at least one or both of an inspiratory limb and expiratory limb. The terms "inspiratory limb" and "expiratory limb" are standard components of most ventilation and anesthesia systems and are thus well known in the art and not further defined herein. In one embodiment, the inspiratory and expiratory portions of the circuit are coaxial and housed in one limb.

Further, the functional system architecture of the CC 102 utilizes a plurality of connections such as regulated supply pressure (e.g. 30 PSI) for $O_2$, $N_2O$ and air, wall suction, electrical power, and data communications (e.g. internal system or hospital network) from the AO 104.

In one embodiment, CC 102 includes a pneumatic connection for respiratory gas that is fed into the system of the present invention via a sample line. CC 102 also includes a pneumatic auxiliary oxygen connection that is directed away from CC 102. In addition, CC 102 includes a pneumatic suction connection to the anesthesia office 104 of the present invention. In one embodiment, CC 102 is electrically connected to physiologic monitoring equipment.

Figure 1C:
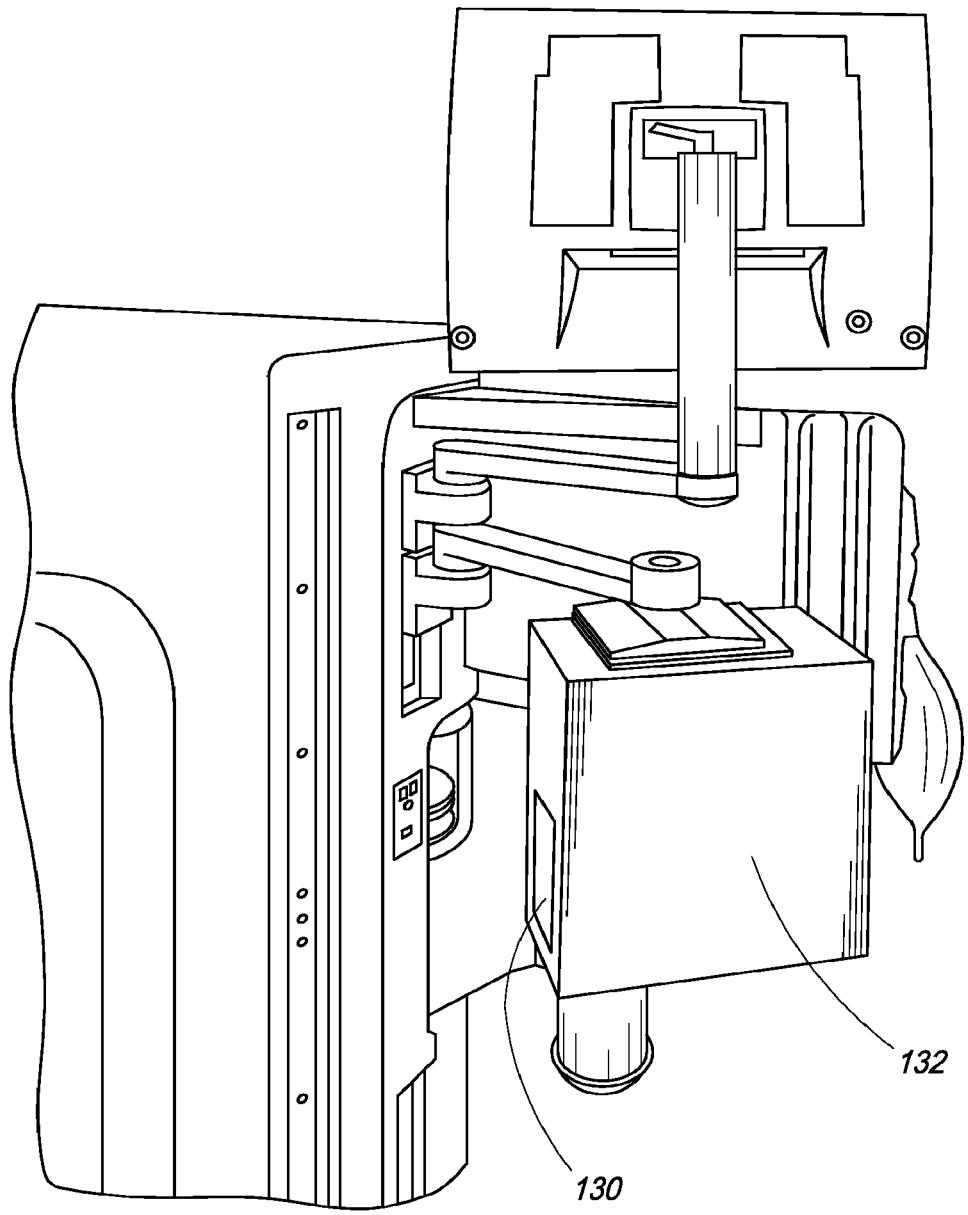
FIG. 1C is a backside illustration of the anesthesia system of the present invention.
Figure 1D:
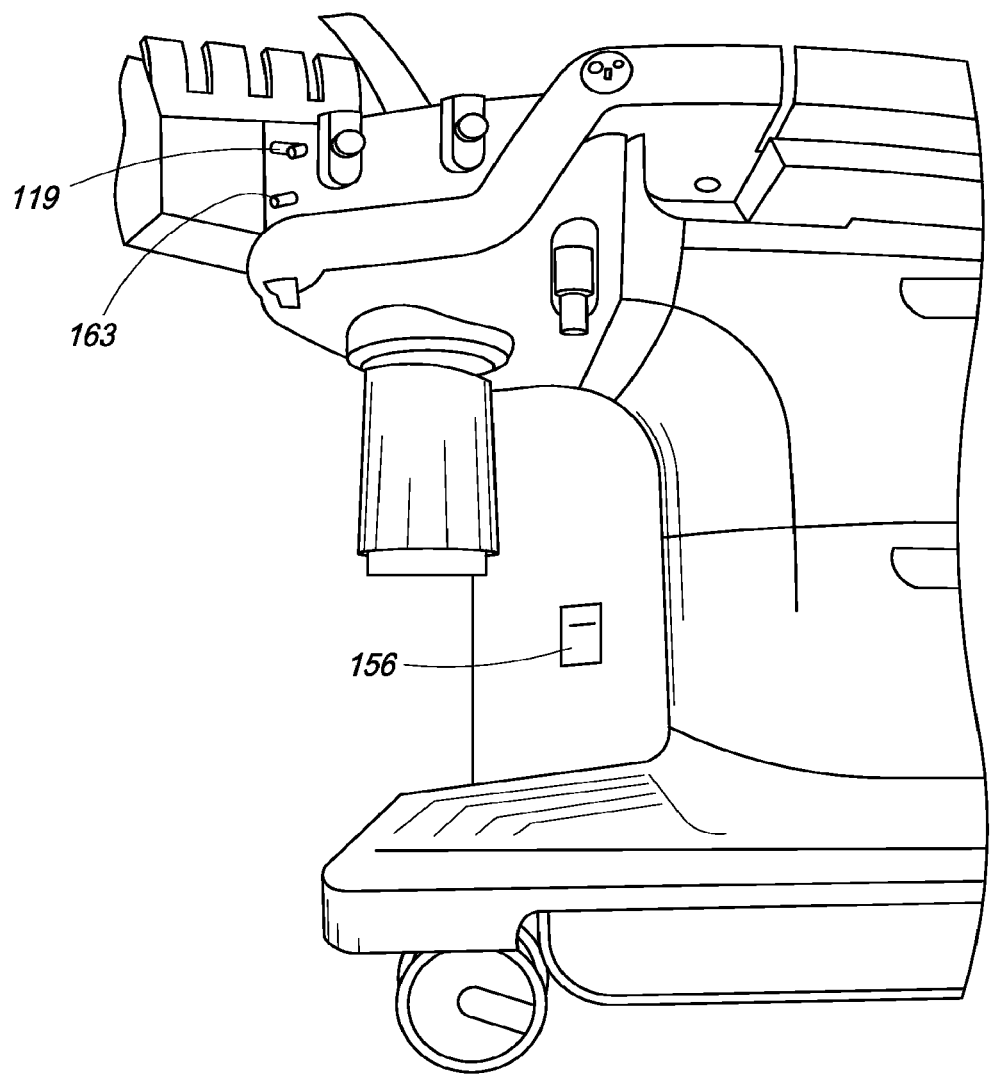
FIG. 1D is a cut-away portion of the anesthesia system of the present invention showing the ventilation monitoring connection, a sample interface for a respiratory gas monitor, and the anesthesia gas scavenging system.

Referring to FIGS. 1A, 1B, 1C, and 1D, CC 102 functionalities and components include a ventilator (not shown) housed in a cabinet 118; ventilator monitoring parameter connections 119; a ventilator display 109; a physiological monitor 132 (shown in FIG. 1C); at least one physiologic monitor display 111; respiratory gas analysis and connections 163 from FIG. 1D; breathing circuit (circle or circleless) and controls 150; common gas outlet (also referred to as Auxiliary Common Gas Outlet) 151; APL Valve 152, Bag 153, and Pressure Gauge 154; Bag to Vent Switch 106; Bellows 107; $CO_2$ Absorber 155; Anesthetic Gas Scavenging 156; Patient Suction Controls 157 and Catheter Storage 158; Auxiliary Oxygen Controls (also referred to as auxiliary Flow Tube) 112 and Connections 113; Fresh Gas Flow Mixing 160 and Controls 161; Vaporizers and Attachment Back Bar 108; Syringe Pump Mounts 116; Expandable Clinical Workspace 115; and Wireless Sensor Docking 117.

Referring back to both FIG. 1A and FIG. 1B, the anesthesia office (AO) 104 is pneumatically connected to CC 102 via a suction supply and anesthesia gas supplies (integrated into the system structure), which include regulated $O_2$, $N_2O$, and air. AO 104 is also pneumatically connected to a wall suction unit, an air pipeline, an $O_2$ pipeline, and an $N_2O$ pipeline. AO 104 is electrically connected to an accessory power source, AC power, and external communication means.

Anesthesia office 104 functionalities and components include user storage areas 120; computer connections and network connections area 125; cylinder attachments (not shown, located behind system), check valves (not shown, integrated into system) and regulation support (not shown, integrated into system); pipeline attachment (not shown, located behind system), check valves (not shown, integrated into system), and regulation (not shown, integrated into system); suction attachment (not shown, located behind system); automatic $N_2O$ shut-off with no $O_2$ (not shown, integrated into system); AC to DC power regulation (not shown, integrated); AC power isolation to accessory connections (not shown, integrated); back-up electrical power systems (not shown, integrated); and a mounting area for $3^{rd}$ party monitoring 170.

Figure 3A:
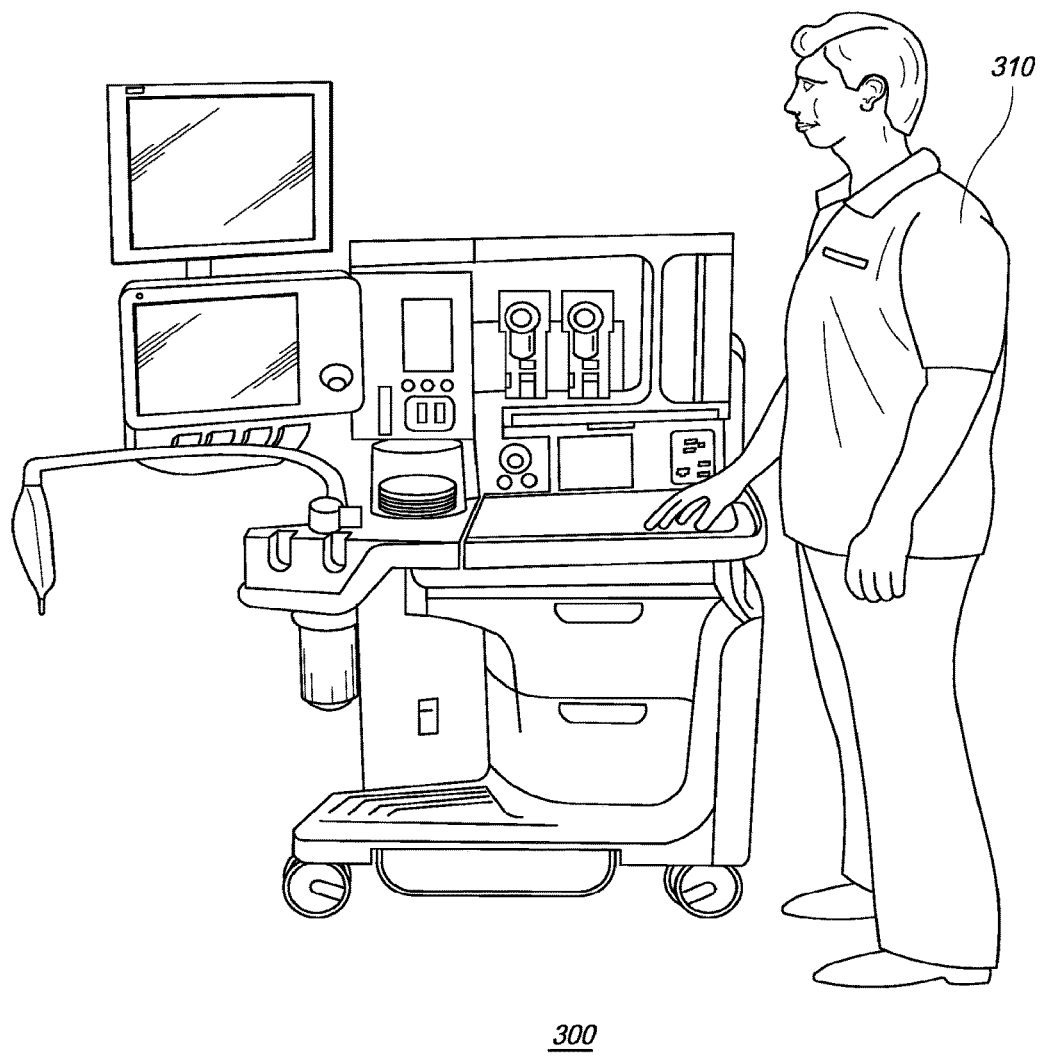
FIG. 3A is an illustration of a clinician standing at the anesthesia system of the present invention.
Figure 3B:
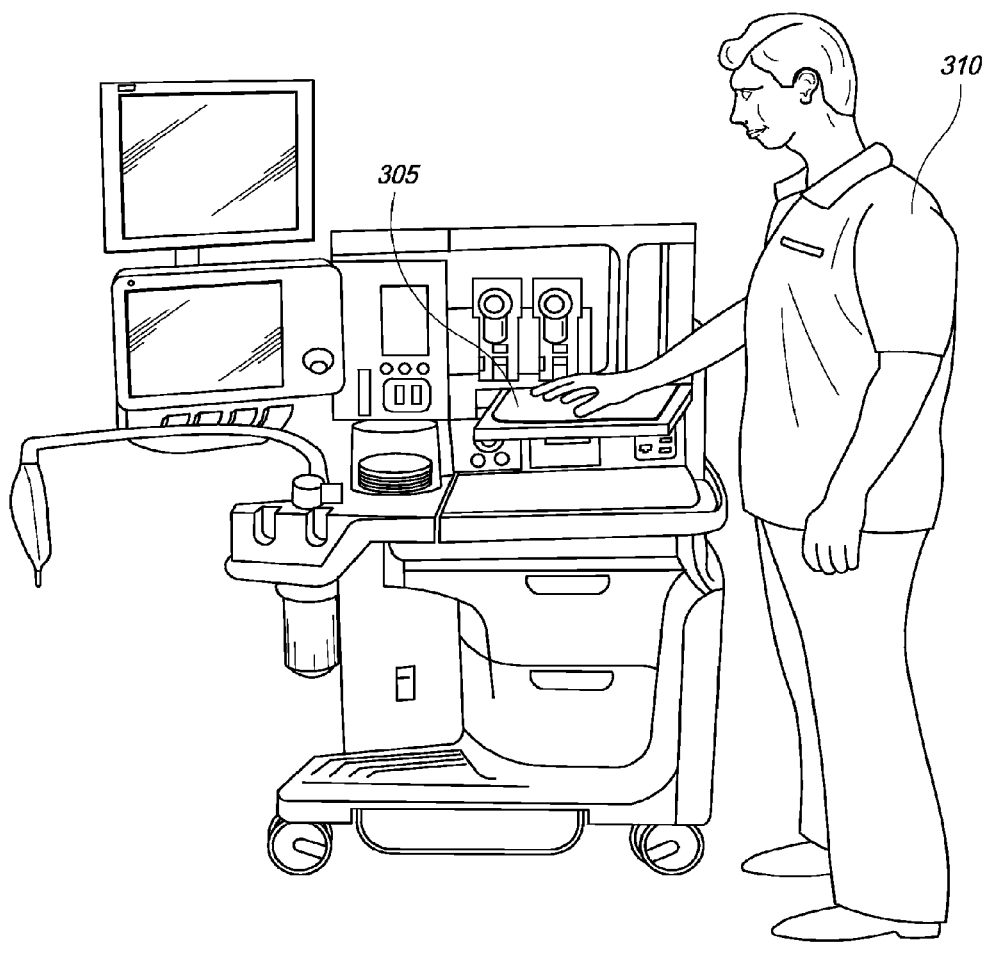
FIG. 3B is an illustration of a clinician standing at the anesthesia system of the present invention, using an upper pull-out shelf as a desk.
Figure 3C:
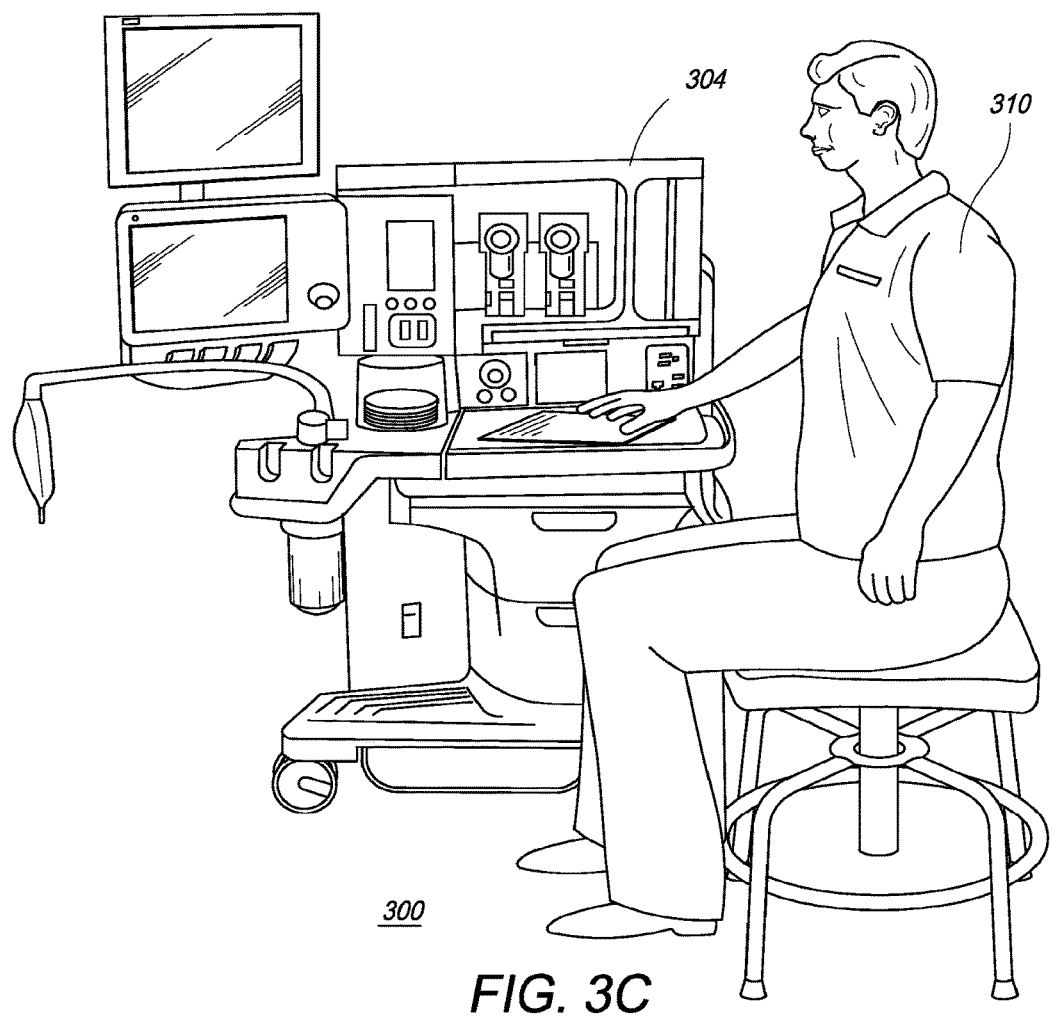
FIG. 3C is an illustration of a clinician sitting at the anesthesia system of the present invention.

In one embodiment, the AO 104 includes a support base for the anesthesia system 100 of the present invention, providing a usable space 171 for the anesthesiologist's documentation, storage 172 and personal effects 173. The AO 104 is equipped with features such as work surfaces 174, 175 to support both the standing and sitting behavior of the anesthesiologist (as shown in FIGS. 3A, 3B, and 3C), pull-out trays 176 that allow for a computer keyboard, medical tape dispenser, personal electrical equipment connectors 178 on the front of the AO, side door storage 177, which, when opened contains easy to clean pockets and cubbies for storage of office items like pens, notes, clipboards, files, etc., foot rest with angled front to allow knee room 179, a handle based caster unlock feature 180 and lighting 181 of work areas for operation in low light conditions.

In one embodiment, the AO 104 houses all pneumatic supplies, AC electrical support and data communication connections for the anesthesia system, and supplies the CC 102 with the necessary inputs for its function. In one embodiment, the AO may be considered the "hub" of the anesthesia system 100 and provides the functions of: AC to DC power conversion for the anesthesia system components including the CC, AC power isolation for accessory outlets, backup power supply (i.e. battery, UPS), pneumatic protection of pipeline sources (i.e. filters, check valves), cylinder attachment and mounting locations, primary regulation of cylinder supplies with automatic pipeline loss cross-over, a system status screen, and hospital network data connections.

FIG. 1C illustrates the backside of one embodiment of the anesthesia system of the present invention, showing a connections area 130, where electrical connections are made to monitoring equipment. Further, as described earlier above, FIG. 1C also shows physiological monitor 132.

FIG. 1D illustrates ventilation monitoring parameter connections area 119 in greater detail. Further, FIG. 1D also shows anesthesia gas scavenging system 156 in enlarged detail. And finally, the figure also shows a sample attachment interface 163 for a respiratory gas monitor.

Referring back to FIG. 1A, several types of movements are available to position the CC 102 relative to the AO 104 in the anesthesia system of the present invention. First, a rotational movement can be used to rotate the breathing circuit 150 (or the CC 102) away from or towards AO 104 at junction 197, in incremental angles up to 45 degrees, such that CC 102 is in a first extended position relative to AO 104.

In one embodiment, the CC 102 is moved on a sliding track (not shown), located on the base support on the AO 104 out from its locked position (i.e. fully integrated position) on the AO 104 into a fully extended position. In one embodiment, a portion of the track is preferably positioned at an oblique angle, which is, in one embodiment 24 degrees, to the front face and wheel base of the AO 104, allowing the movement of the CC 102 and its connection ports to move forward and left from its fully integrated position.

Second, a translational movement at junction 196 having a range of 0 to 14.5 inches is available to compress and collapse the CC 102 back into AO 104 or extend CC 102 away from AO 104. In addition, the translational movement at junction 196 also results in translational movement at junction 197. Thus, once translated away from AO 104, CC 102 is in a second extended position relative to AO 104.

In addition, the aforementioned rotational and translational movements can be combined, such that CC 102 is in a third extended position relative to AO 104.

It should be evident to those of ordinary skill in the art, that although only a few positions are shown, CC 102 can have a plurality of positions relative to the AO 104. In one embodiment, the workspace point (shown as 297 in FIG. 2A and described in greater detail below) can be accessed by rotating, translating, or both rotating and translating CC 102 away from AO 104.

Figure 2A:
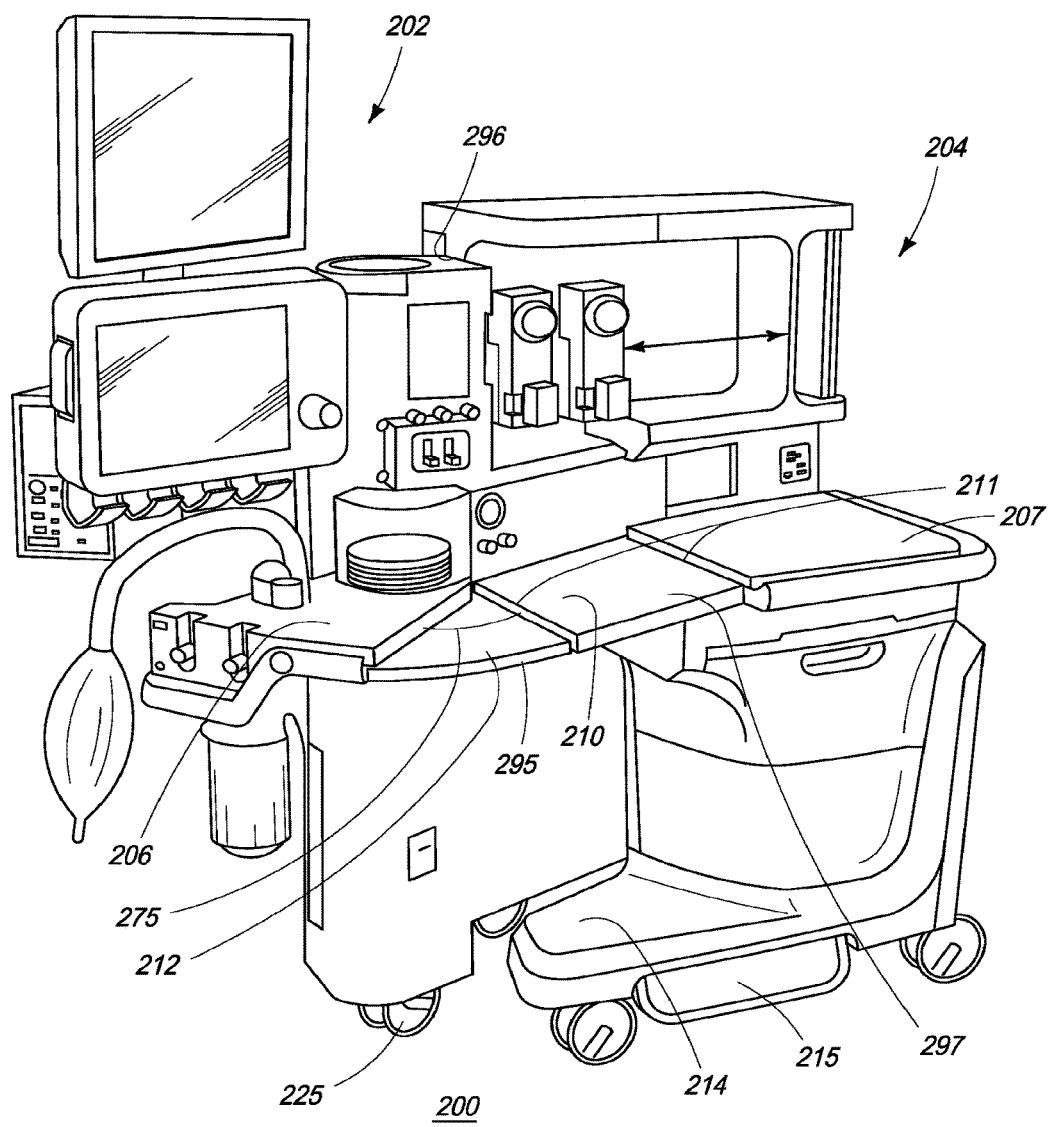
FIG. 2A is an illustration of the anesthesia system of the present invention in a first configuration, fully rotated and telescoped.

FIG. 2A illustrates the CC 202 telescoped outwards and away from the AO 204, creating a clinical workspace area for the clinician's use. By way of comparison, and referring back to FIG. 1A, the anesthesia system 100 of the present invention shown in FIG. 1A is in a fully collapsed position. Referring back to the telescoped system 200 in FIG. 2A, the gap created as the CC 202 moves away from the AO 204 expands and exposes work surface 210 such that it extends out from areas under the main AO work surface 207. These surfaces 210 have close tolerance or flexible seals at their interfaces 211 to avoid having materials sitting on the surfaces being jammed into the gap between surfaces. In an embodiment, the movement of the CC 202 is indexed in order to create a rigid positioning means for the CC 202 relative to the AO 204. In other embodiments a plurality of other locking means not involving indexing could also be utilized, in order to obtain a locking mechanism rigid enough to prevent inadvertent movement of the CC 202 relative to the AO 204, and the dislodging of articles on the expanded work surface 210.

In yet another embodiment, the CC 202's movement relative to the AO 204 is motorized and is actuated electronically by user controls on the anesthesia system 200. In an example, a single user actuation results in a preprogrammed motorized movement of the CC 202 relative to the AO 204. In an embodiment, if the user-actuated motorized movement of the CC 202 encounters an obstruction, the movement of the CC 202 is automatically stopped. In one embodiment the change in electric current drawn by the movement motor is utilized to detect obstruction. At the same time, in additional or alternative embodiments, obstruction signals in the form of audio alarm and/or visual alarms, such as a flashing light is used to indicate obstruction (to user) and the resulting stalled movement of the CC 202. In one embodiment, existing lights used for illuminating various elements of the anesthesia system are utilized as alarm flashing lights. Examples of such existing lights comprise those in the overhead area near point 196 in FIG. 1A focusing on the vaporizers and/or the work surface that is proximal to point 197 of FIG. 1A.

Further, FIG. 2A illustrates at least one floor contact point 225 at the bottom of the CC 202. As the CC 202 moves a considerable distance away from the AO 204 and the main four wheel trolley base 214, it is not practical to cantilever the CC 202 part of the system from the AO 204, due to tip and strength concerns. Consequently, the CC 202 employs its own ground contact point 225 to allow for load-bearing, which may include one or more users leaning on the CC 202, to be transferred directly to the floor rather than through the AO 204 trolley frame.

In one embodiment, the at least one contact point 225 is capable of providing equal horizontal friction in a full 360 degree pattern and is, but is not limited to, a rotating trackball type or caster wheel type (having multiple rollers) of moveable load transfer mechanism that enables both inline and side to side movement. The use of a moveable contact ensures that the CC 202 and the anesthesia system 200 can be moved or relocated in its entirety and quickly, even in an "open" or fully extended configuration. In an embodiment, the anesthesia system 200 is locked using a central brake system that locks either two or four of the wheels under the AO 204. This central brake system, is, in one embodiment, controlled via a foot pedal 215, known to those of ordinary skill in the art, or may be controlled via a hand lever positioned in one or more locations on the anesthesia system's movement handles, which is described in greater detail below. The hand lever provides a more direct lock/unlock arrangement.

In one embodiment, the at least one contact point 225 is disengaged from the floor when the CC 202 is moved into its base, locking position against the AO 204, leaving just the original, standard four casters in contact with the floor. Alternatively, the contact between the CC 202 and the floor could be maintained even in the locked position. In one embodiment, the contact point 225 is configured with the appropriate geometry to move obstructions on the floor as the contact point 225 is extended, including, but not limited to elements such as a cover or flexible spring that comes in close proximity to the floor and thereby pushes or lifts obstructions prior to these obstructions getting close to the contact points 225 on the floor.

Thus, in various embodiments, the floor contact point and movement mechanisms of the CC allow for load bearing to the workspace area created by its movement away from the AO, with no risk of tipping or damage. The additional usable workspace exposed by the separation of the CC from the AO, described below, may be used by the clinician for their supplies and tools, solving the issue of "limited workspace" on smaller machines. Subliminally, this also allows the anesthesiologist to establish "their space" in what can be a very crowded OR environment containing many people and varieties of equipment. This space allows them to separate their clinical responsibilities and workflow from those that are more documentation and office related.

FIG. 2A illustrates an angular articulation of the breathing circuit connection area 206 away from the AO 204. The breathing circuit connection area 206 is both telescoped and rotated outwards, and a "cockpit" area is generated for the clinician, with the AO 204 on the right hand side and the CC 202 sweeping to the left. In this configuration, the AO 204 can advantageously be positioned well away from the patient and out of the clinical field, but the CC 202, with all the clinical controls can be positioned in close proximity to the patient. It is observed that the additional angular rotation of the breathing circuit area 206 also exposes additional workspace 212 for the clinician.

In various embodiments of the present invention, the telescopic motion and angular rotation movements of the anesthesia system and its components can be deployed in a variety of configurations allowing the CC 202 to be positioned at a plurality of locations relative to the AO 204. As mentioned above with respect to FIG. 1A, three types of movements are available to position the CC 202 relative to the AO 204 in the anesthesia system of the present invention.

Figure 2B:
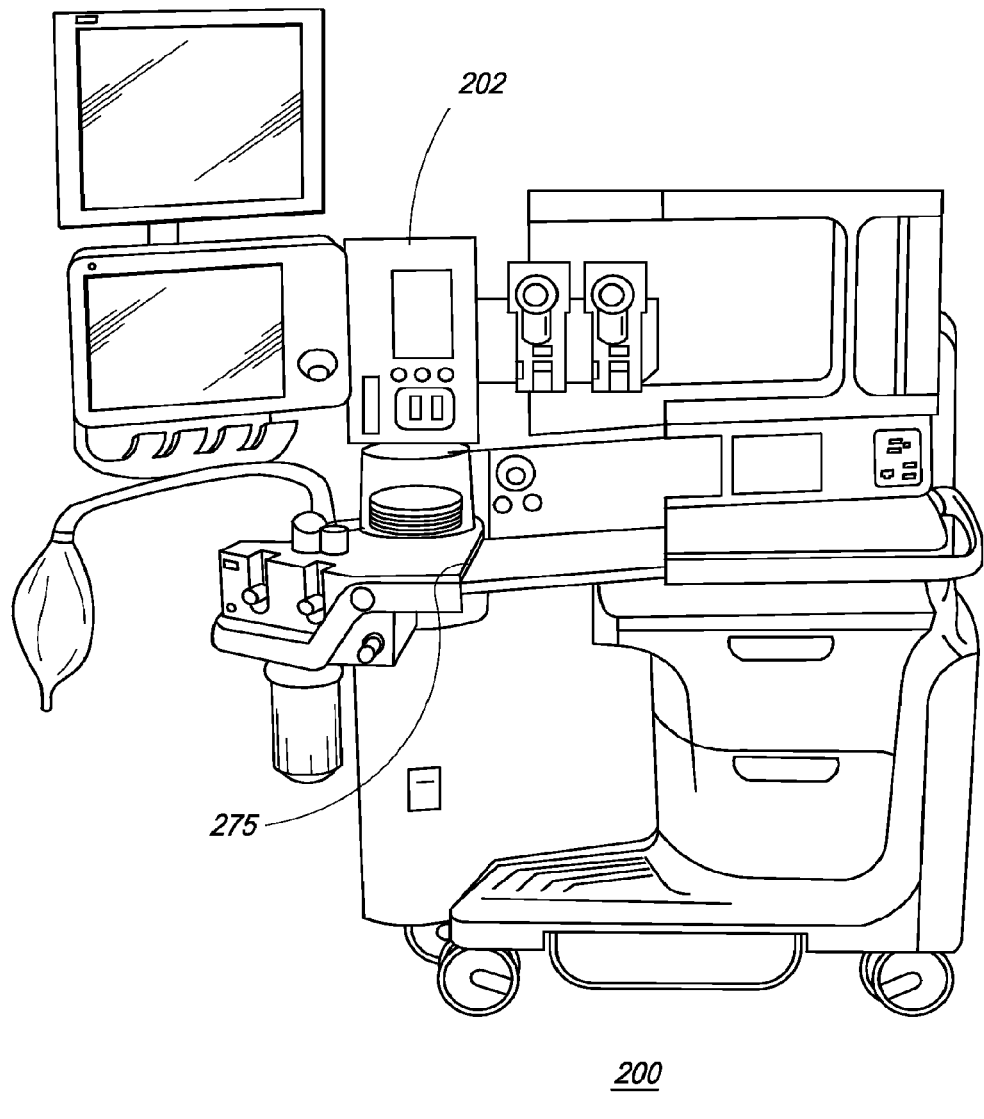
FIG. 2B depicts the anesthesia system of the present invention in a second configuration, fully telescoped, but not rotated.

In one embodiment, a rotational movement can be used to rotate CC 202 away from or towards AO 204 at junction 295, in incremental angles. FIGS. 2A and 2B depict the anesthesia system of the present invention in various configurations. FIG. 2A begins with the anesthesia system 200 of the present invention in a fully extended and rotationally open position, with the rotational angle 275 in a fully open position of 45 degrees. Angle 275 is rotated from a maximum of 45 degrees to a minimum of zero degree, in increments, until the CC portion 202 of the anesthesia system 200 is in a rotationally closed or collapsed position and is thus rotationally flush with the system, with angle 275 at zero degrees, as shown in FIG. 2B. In one embodiment, the rotational increments are indexed at preset angles, such as at every 5 degrees, or controlled continuously using a friction bearing to be any selected angle. In a preferred embodiment, there is a detent at the zero degree angle (that is, closed or collapsed position of system 200) so that when the system 200 is rotated fully closed it "clicks" shut in a positive manner.

Figure 2C:
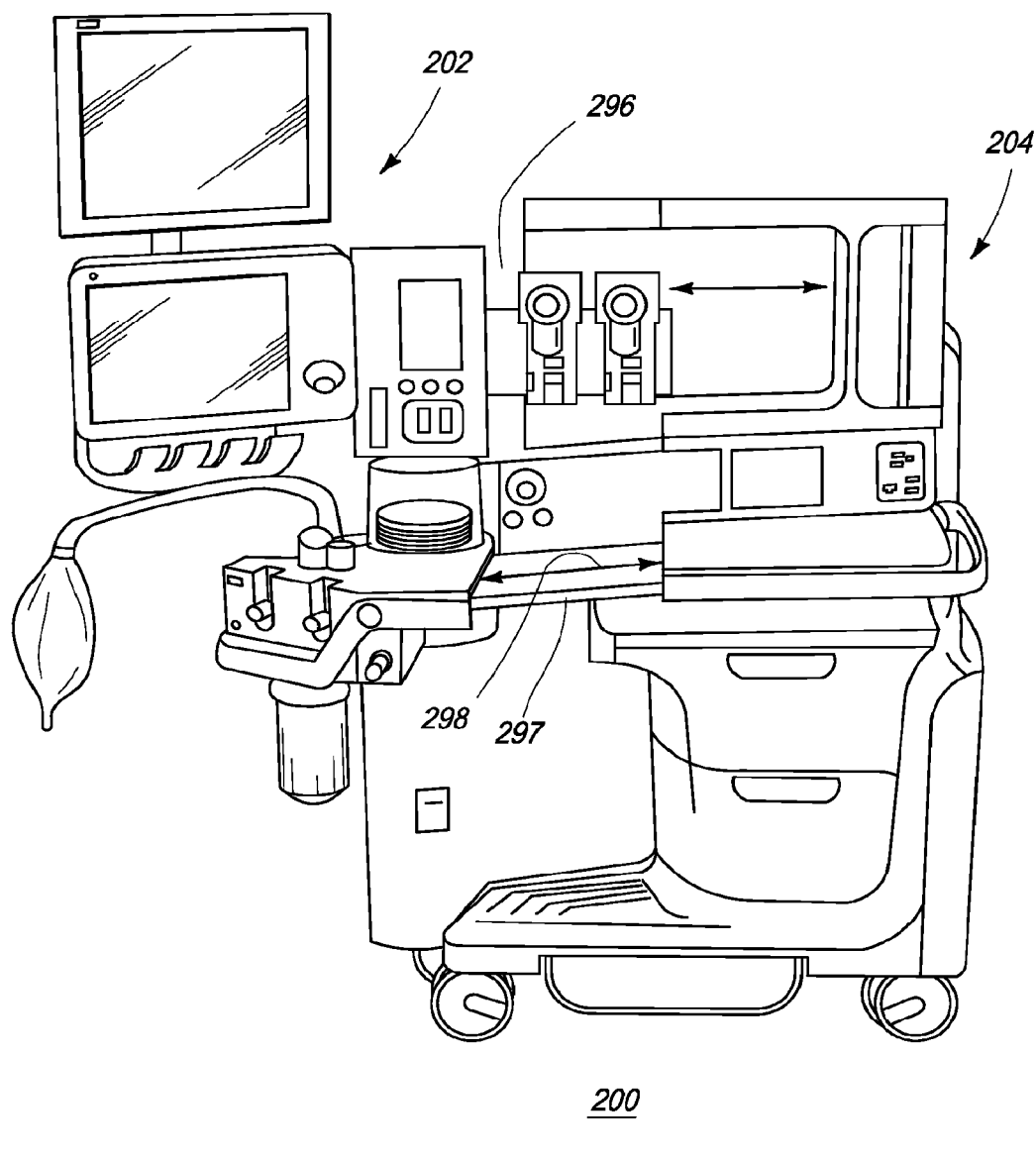
FIG. 2C depicts the movement of anesthesia system of the present invention in a third configuration, as the CC is compressed and collapsed back into the AO and thus in a partially telescoped position.
Figure 2D:
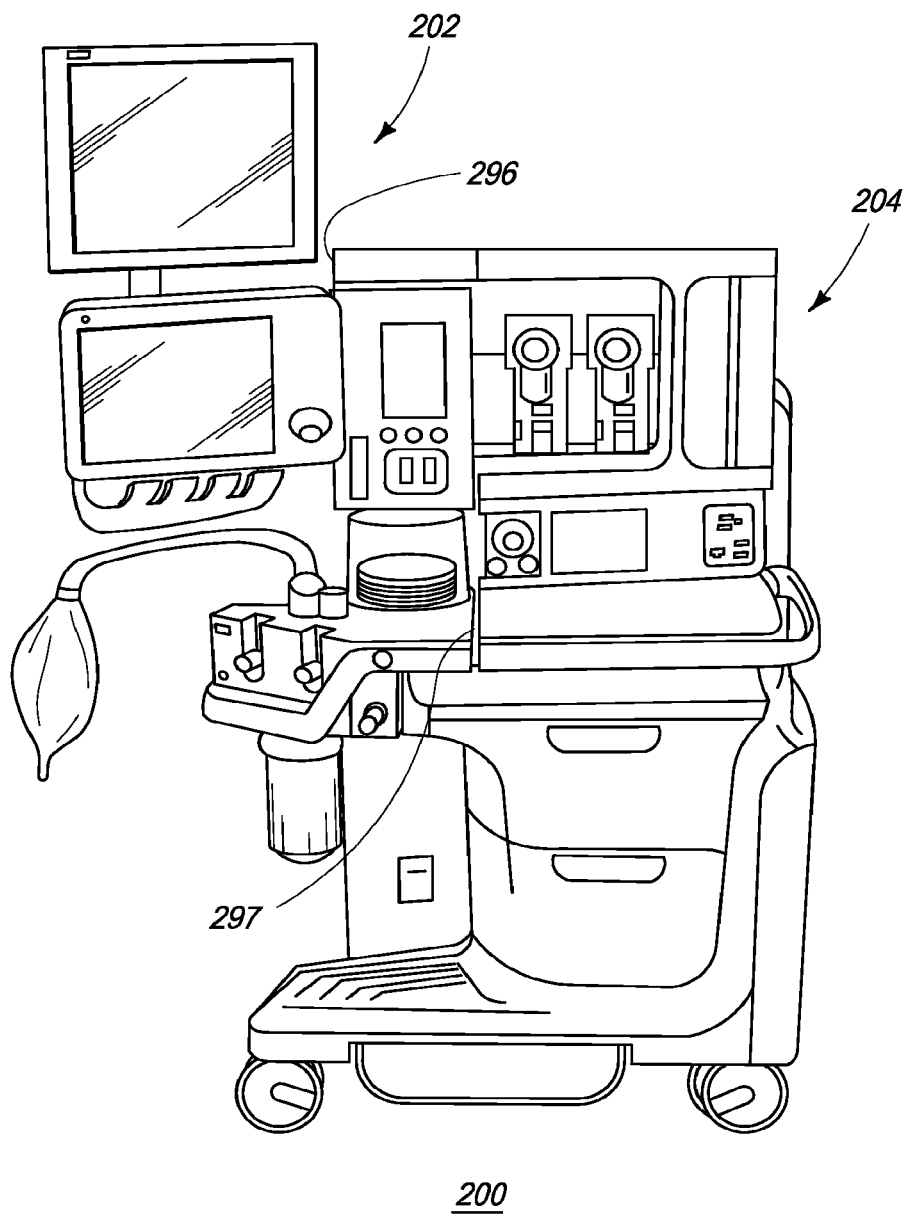
FIG. 2D depicts the movement of anesthesia system of the present invention in a fourth configuration, as the CC is compressed and collapsed back into the AO and thus in a fully collapsed position.

In another embodiment, a translational movement at junction 296 is available to telescopically or linearly compress and collapse the CC 202 back into AO 204 or extend CC 202 away from AO 204. FIGS. 2C and 2D depict the range of translational movement of the system 200 at junction 296 as the CC 202 is compressed and collapsed back into the AO 204. In one embodiment, the translational movement range available to compress and collapse CC 202 back into the AO 204 is 14.5 inches. It should be noted herein that a translational movement at point 296 also results in a translational movement 298 at junction 297.

Figure 2E:
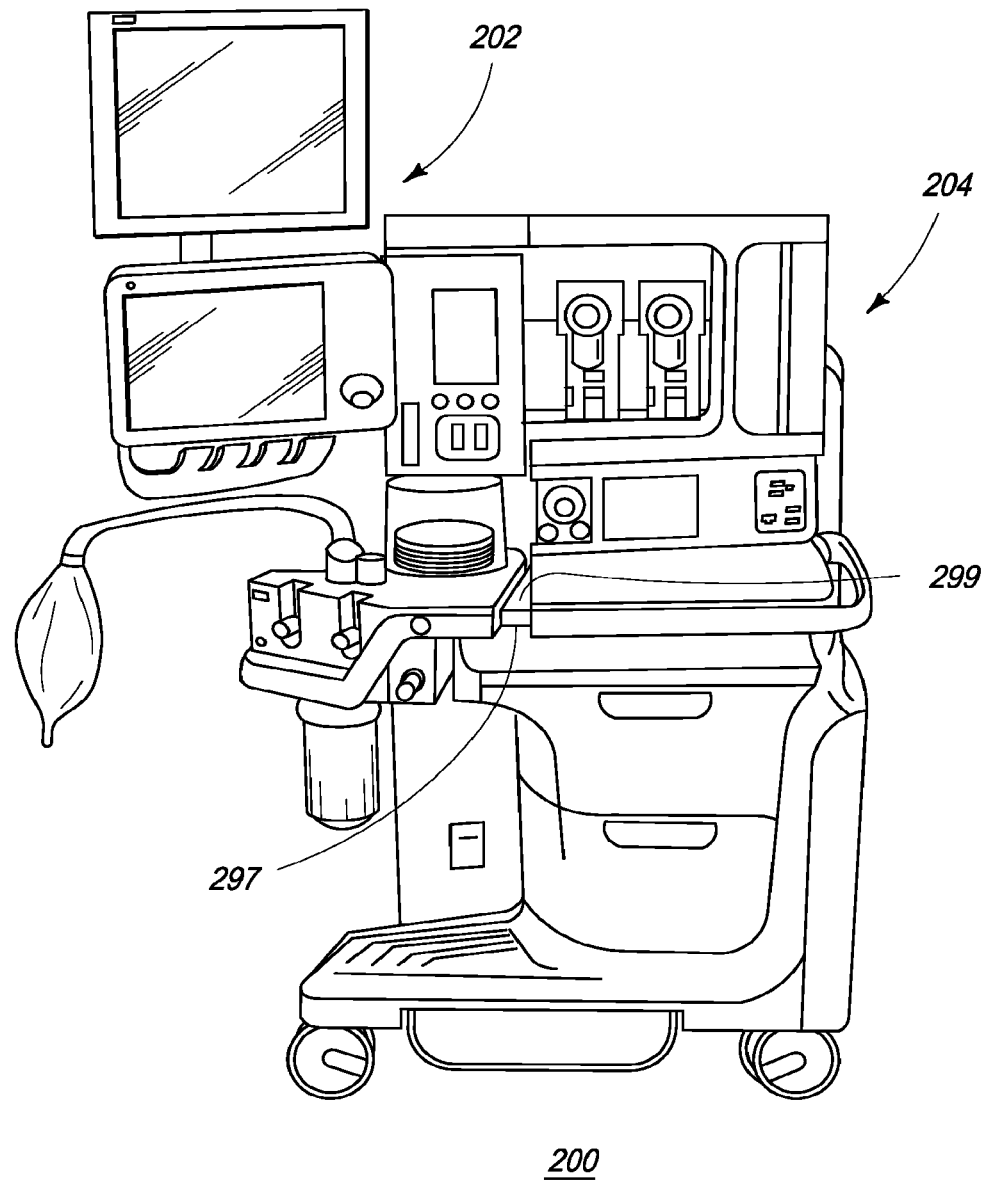
FIG. 2E depicts the incremental angular motion of the CC as it is partially rotated away from the AO, in a fifth configuration.
Figure 2F:
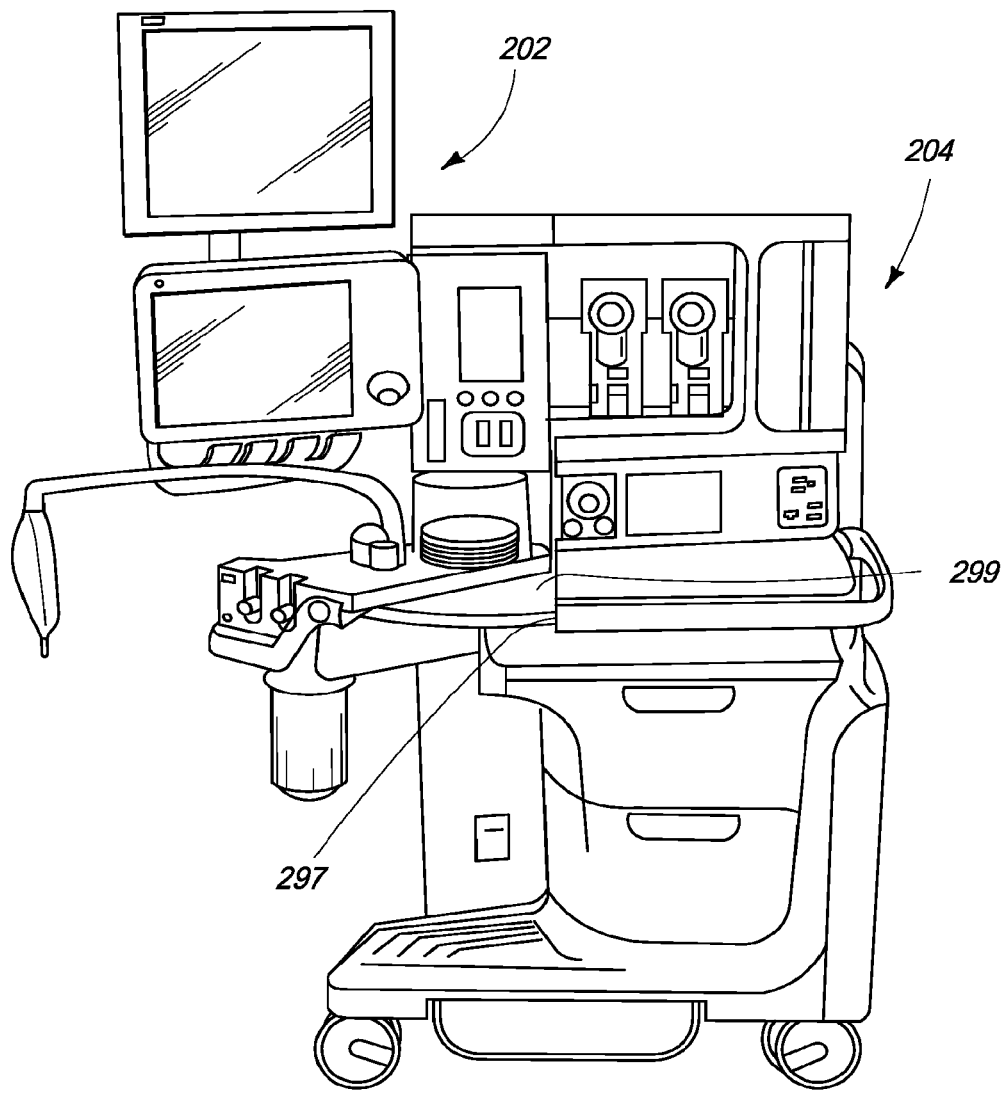
FIG. 2F depicts the incremental angular motion of the CC as it is fully rotated away from the AO, in a sixth configuration.

It should be appreciated by those of ordinary skill in the art that the rotational and translational movements can be combined to have a plurality of positions of the CC 202 relative to the AO 204. Thus, in one embodiment, a workspace 299 can be accessed by either rotating or translating CC 202 away from AO 204 at junction 297, as shown in FIGS. 2E and 2F. FIG. 2E depicts the angular motion of the CC 202 as it is moved in at least one increment, away from AO 204, at an angle of, for example, 5 degrees. FIG. 2F depicts the angular motion of the CC 202 as it is fully rotated away from AO 204 at an angle of 45 degrees, in accordance with one embodiment, but when the anesthesia system 200 has not been expanded or telescoped for extra workspace. In addition, the CC may be telescoped out from the AO (translational motion), creating or exposing additional workspace, as described above.

Hence, in various embodiments the CC of the anesthesia system of the present invention may be unilaterally moved towards a patient and away from the main trolley apparatus containing the AO, cylinders and pipeline gas connections. Since, the CC carries all clinical controls and visual displays necessary for the clinician's direct treatment of the patient, these areas remain within easy reach and sight of the clinician addressing the patient. The resulting system architecture eliminates the need for external connections to the CC and requires only "clean" pneumatic pipeline and power supplies to be provided. In one embodiment, the CC itself could be utilized as a small anesthesia system, utilizing a longer umbilical to electrical and pneumatic sources.

FIG. 3A is an illustration of a clinician 310 standing near the anesthesia system 300 of the present invention. Thus, in this illustration, one can see the relative dimensions of the system with respect to the clinician 310. FIG. 3B illustrates the clinician 310 using an expandable pull-out shelf 305 located on system. FIG. 3C illustrates the clinician 310 sitting at the AO portion 304 of the system 300, when it is in a fully collapsed configuration.

Figure 4A:
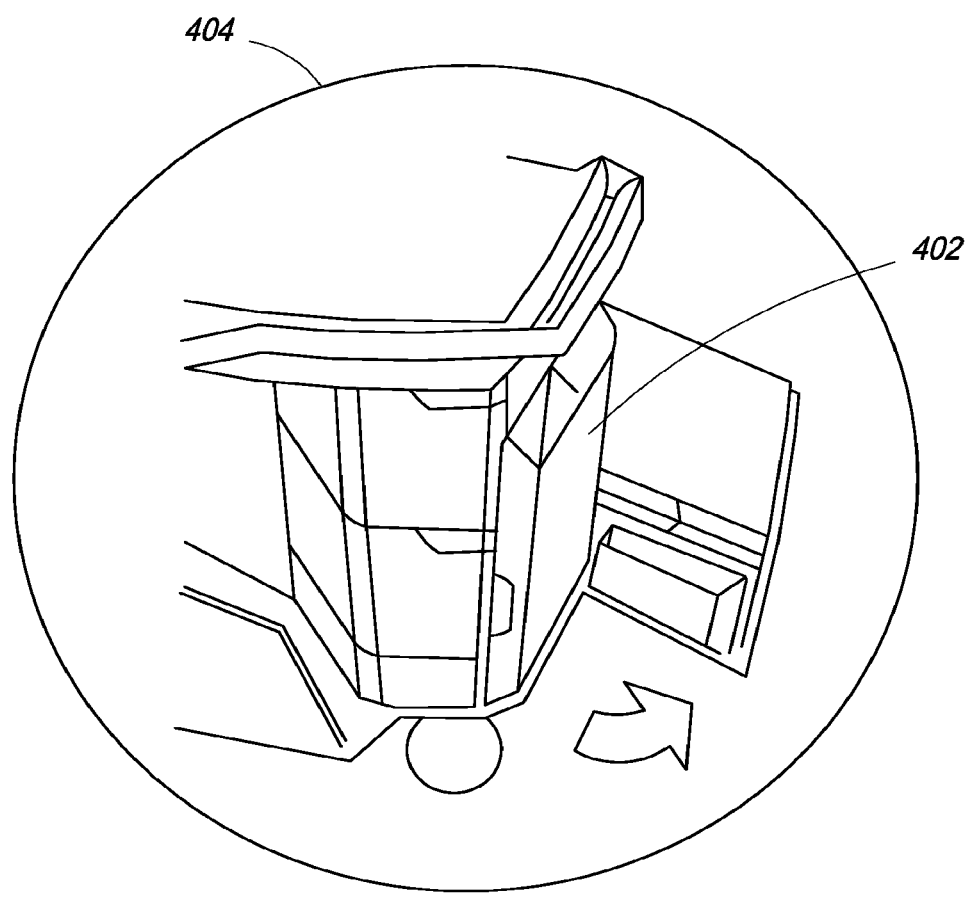
FIG. 4A is a schematic drawing of a side door storage integrated with the anesthesia system of the present invention.
Figure 4B:
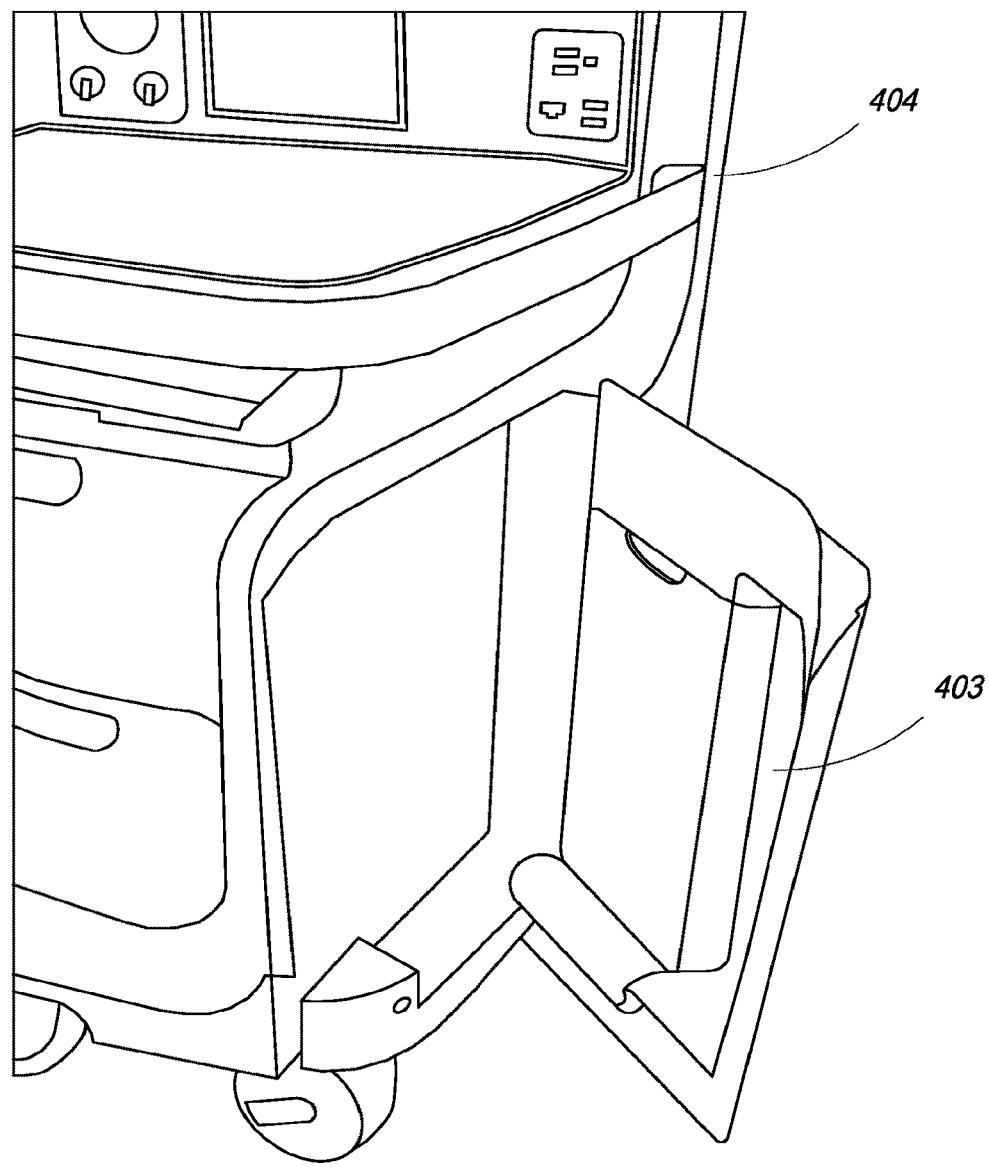
FIG. 4B is an illustration of an open side door storage area of the anesthesia system of the present invention.
Figure 4C:
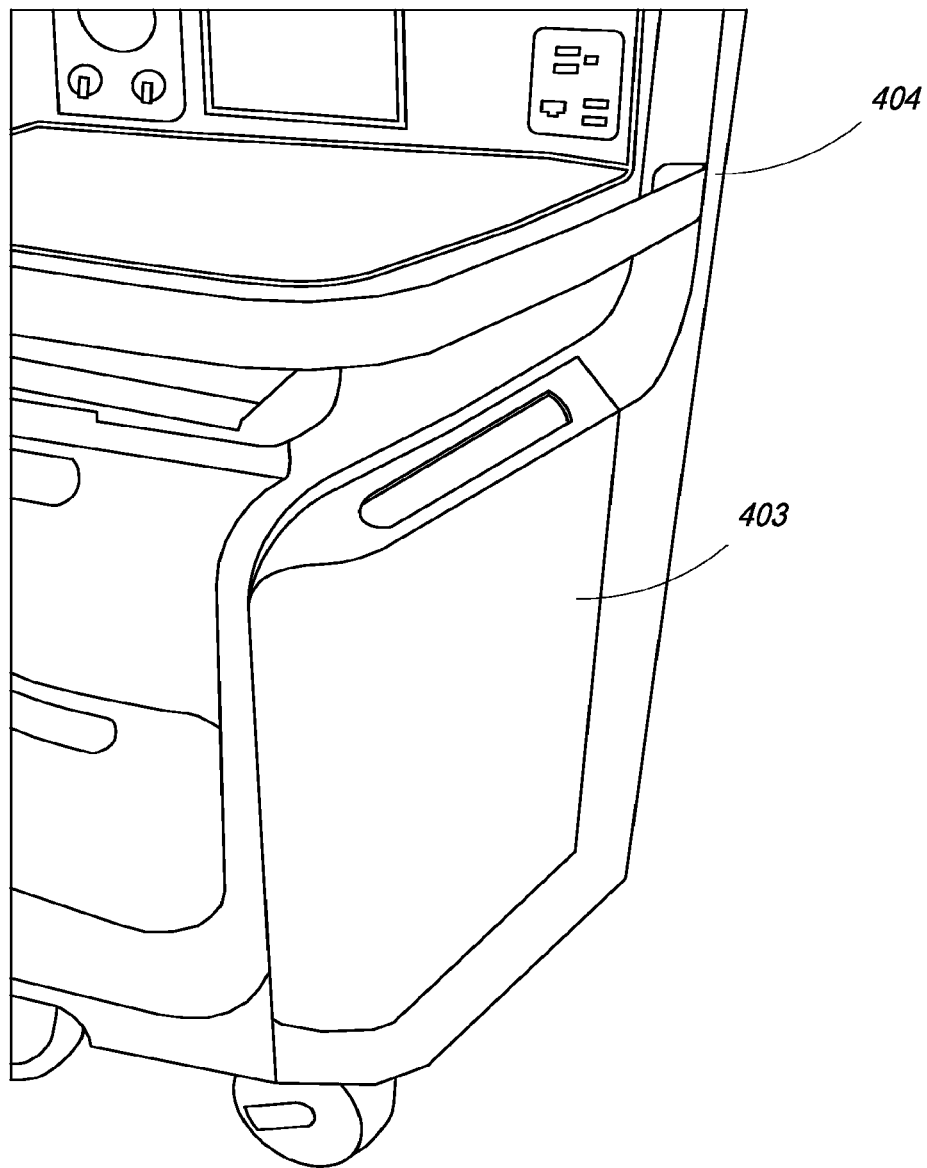
FIG. 4C is an illustration of a closed side door storage area of the anesthesia system of the present invention.

FIG. 4A illustrates the side storage 402 provided in the AO 404 in accordance with an embodiment of the invention. The side storage 402 may be used by a clinician to store odd shaped and longer items that would not typically fit well in storage drawers. FIG. 4B is an illustration of the side storage door 403 in an open configuration. FIG. 4C is an illustration of the side storage door 403 in a closed configuration.

Figure 5A:
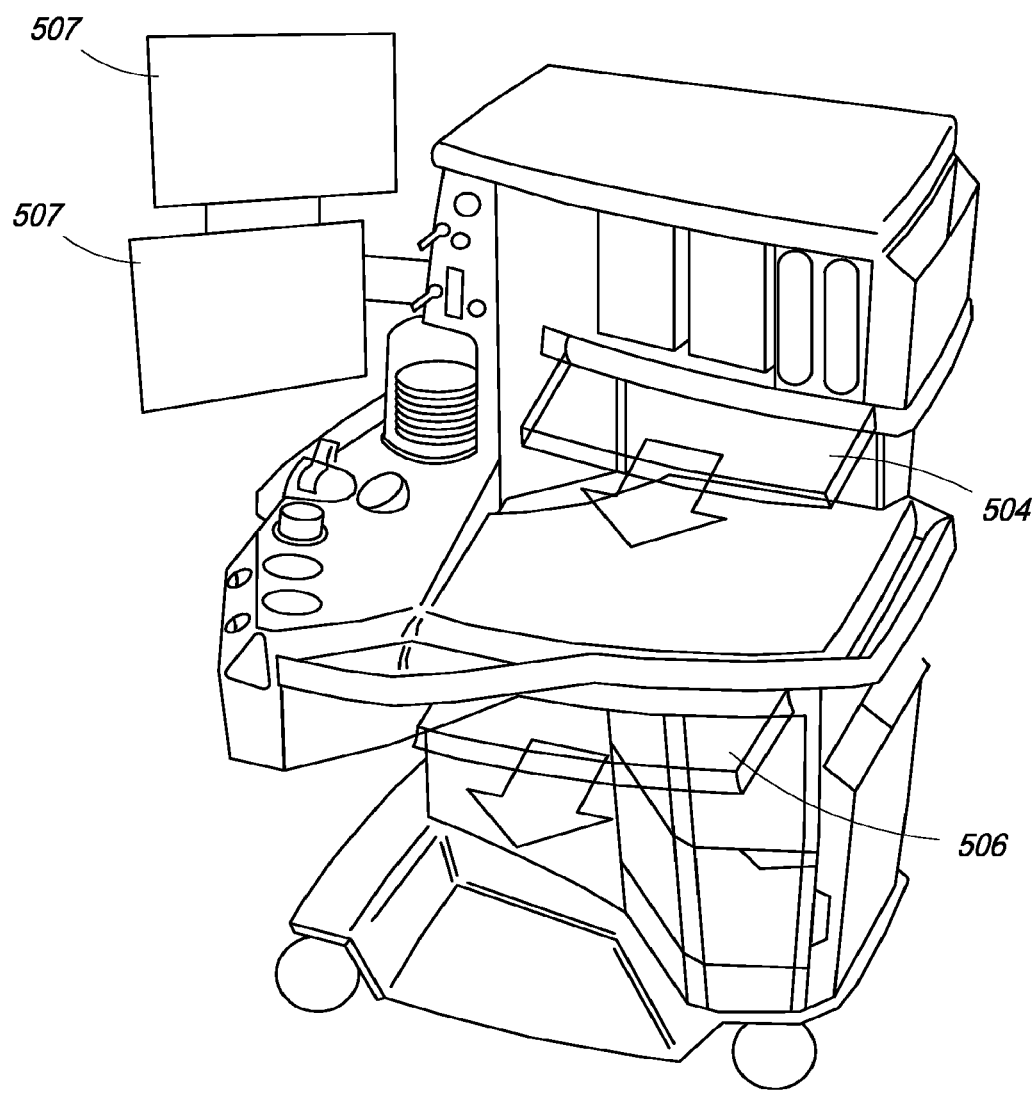
FIG. 5A is a schematic drawing of an upper and lower pull out shelf integrated with the anesthesia office portion of the anesthesia system of the present invention.

FIG. 5A illustrates pull-out shelves in the AO in accordance with an embodiment of the invention. Pull/slide-out shelves/trays 504 and 506 are provided at different heights and can be used for a plurality of purposes such as for placing a computer keyboard. Further, also shown in FIG. 5A is at least one moveable monitor screen or display 507.

Figure 5B:
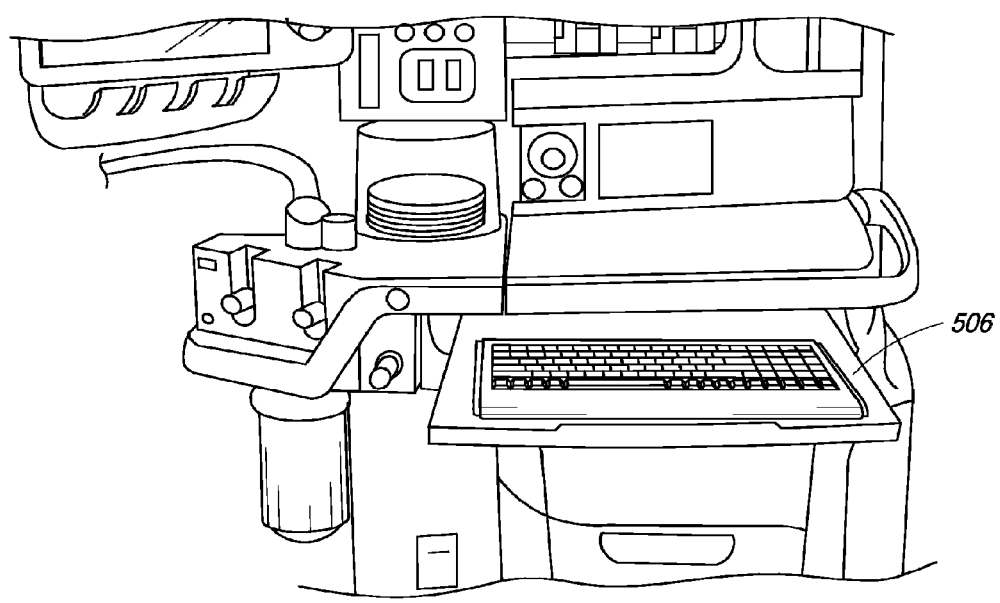
FIG. 5B is an illustration of a lower pull out shelf integrated with the anesthesia office portion of the anesthesia system of the present invention, in an open position.
Figure 5C:
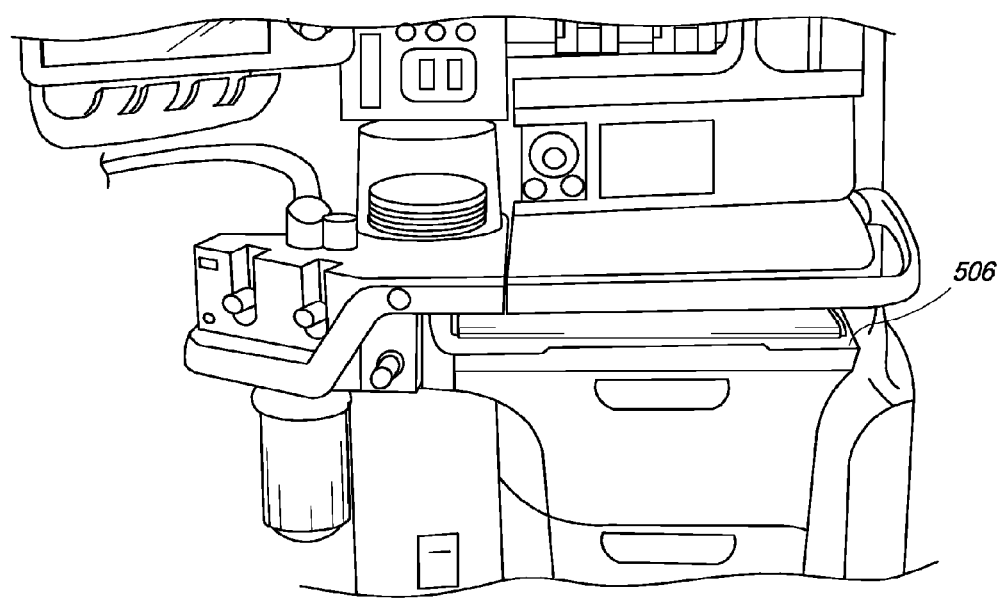
FIG. 5C is an illustration of a lower pull out shelf integrated with the anesthesia office portion of the anesthesia system of the present invention, in a stowed position.

FIG. 5B illustrates lower pull-out shelf 506, when it is pulled out of the AO of the system, further showing a keyboard on the pull-out shelf FIG. 5C shows the lower pull-out shelf 506 in a hidden configuration, when it is stowed into the AO of the system.

Figure 5D:
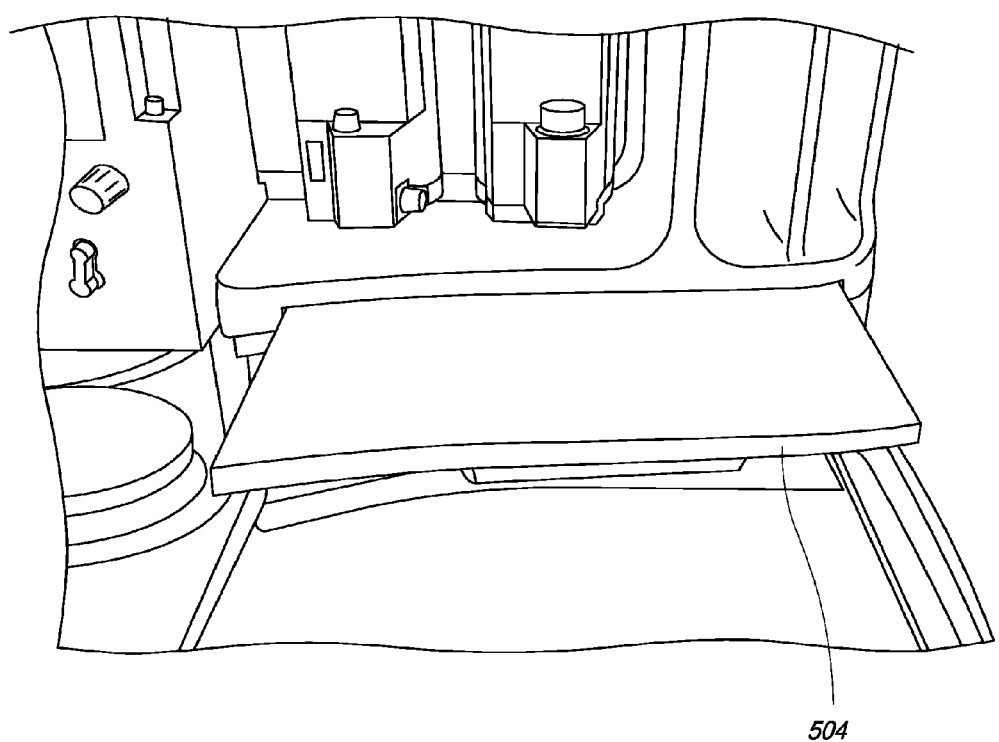
FIG. 5D is an illustration of an upper pull out shelf integrated with the anesthesia office portion of the anesthesia system of the present invention, in an open position.
Figure 5E:
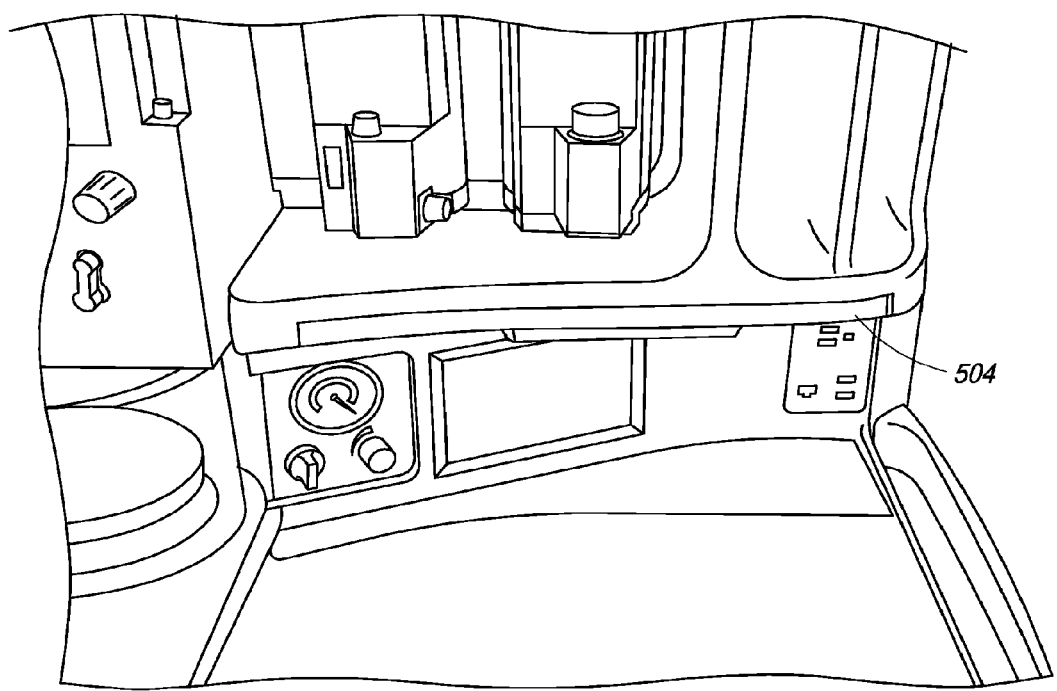
FIG. 5E is an illustration of an upper pull out shelf integrated with the anesthesia office portion of the anesthesia system of the present invention, in a stowed position.

FIG. 5D illustrates upper pull-out shelf 504, when it is pulled out of the AO of the system. In one embodiment, upper pull-out shelf can be used as a writing desk for the clinician to take notes while he or she is standing. FIG. 5E shows upper pull-out shelf 504 in a stowed or hidden configuration.

Figure 6A:
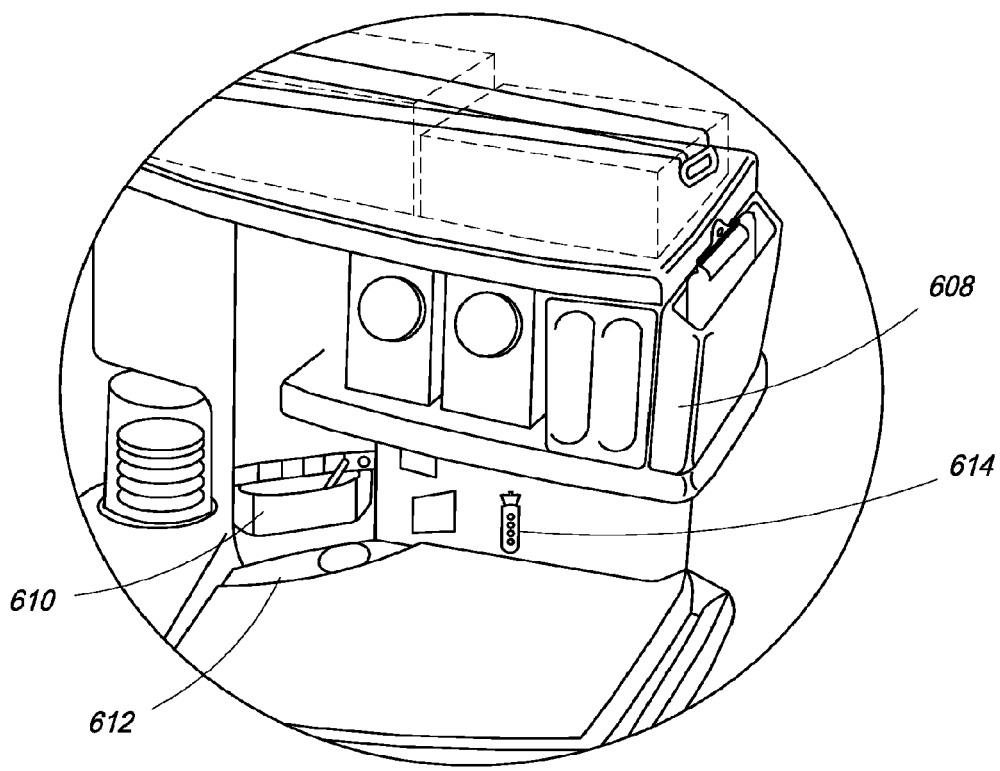
FIG. 6A is a schematic drawing of storage and electrical connection areas integrated with the anesthesia office portion of the anesthesia system of the present invention.
Figure 6B:
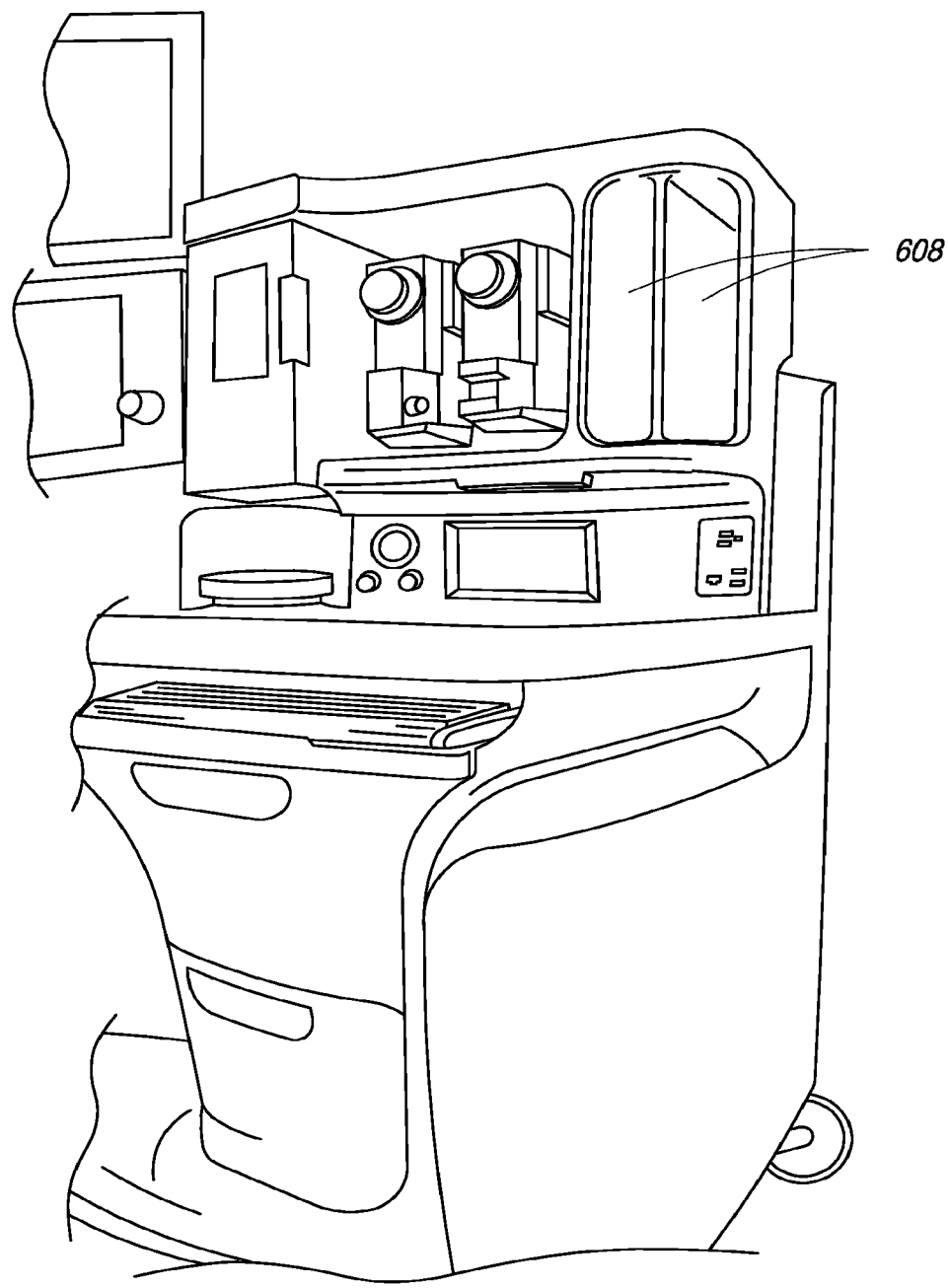
FIG. 6B is an illustration of a storage area integrated with the anesthesia office portion of the anesthesia system of the present invention.
Figure 6C:
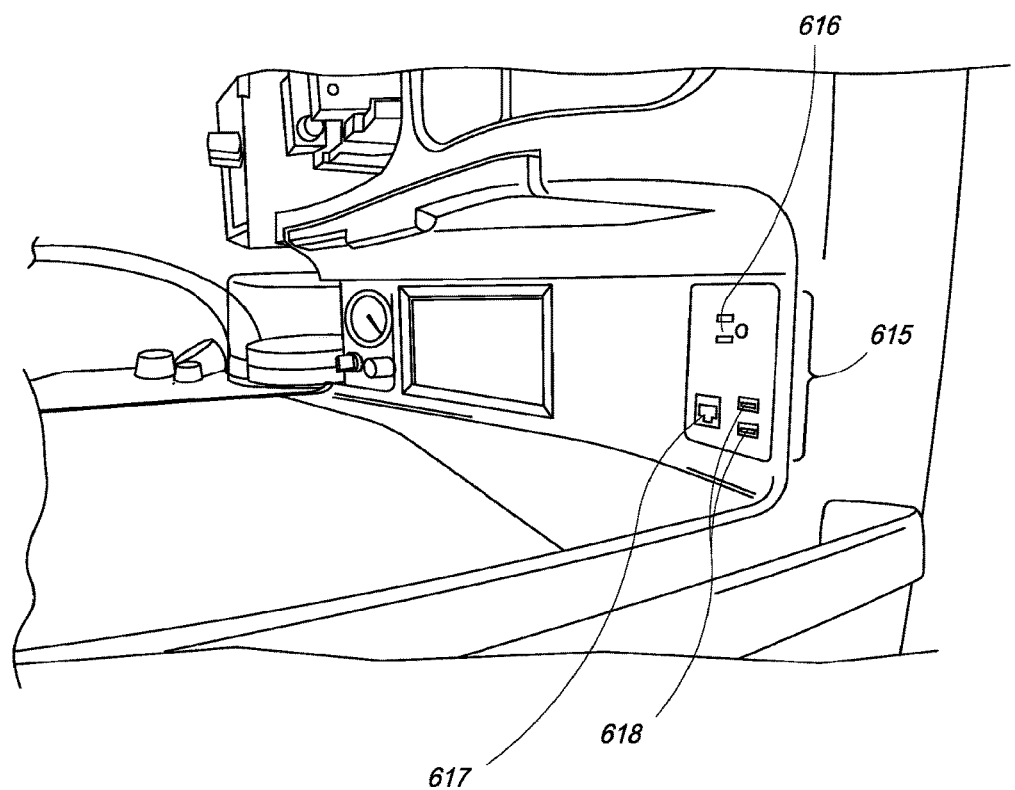
FIG. 6C is an illustration of a electrical connection area integrated with the anesthesia office portion of the anesthesia system of the present invention.

FIG. 6A illustrates space provided for storage and for electrical connections in the AO in accordance with an embodiment of the invention. In one embodiment, storage cubbies 608 and 610 may be used for storage of office items like pens, notes, clipboards, files, etc. The electrical connectors 612 and 614 may be used by clinicians for connecting their personal electronic devices. FIG. 6B is a further illustration of storage cubby 608. FIG. 6C is an illustration of one embodiment of an electrical connection area 615, which may include three-prong outlet 616, Ethernet port 617, and at least one USB port 618.

Figure 7A:
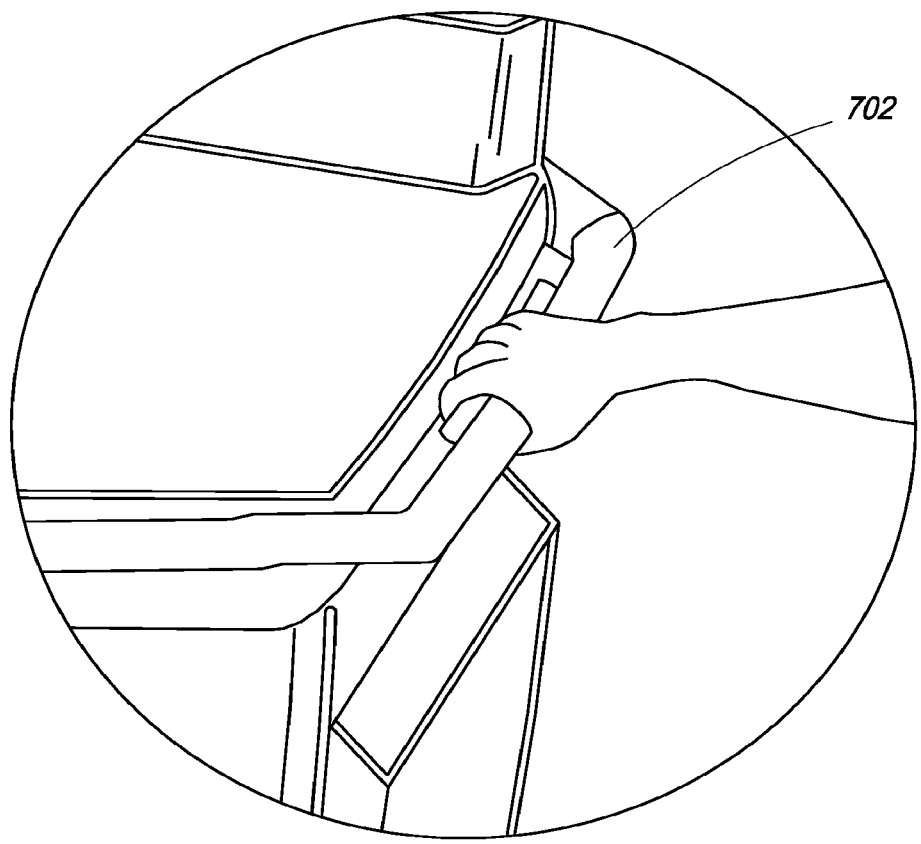
FIG. 7A is a schematic drawing of a handle activated castor lock provided in the AO in accordance with an embodiment of the invention.
Figure 7B:
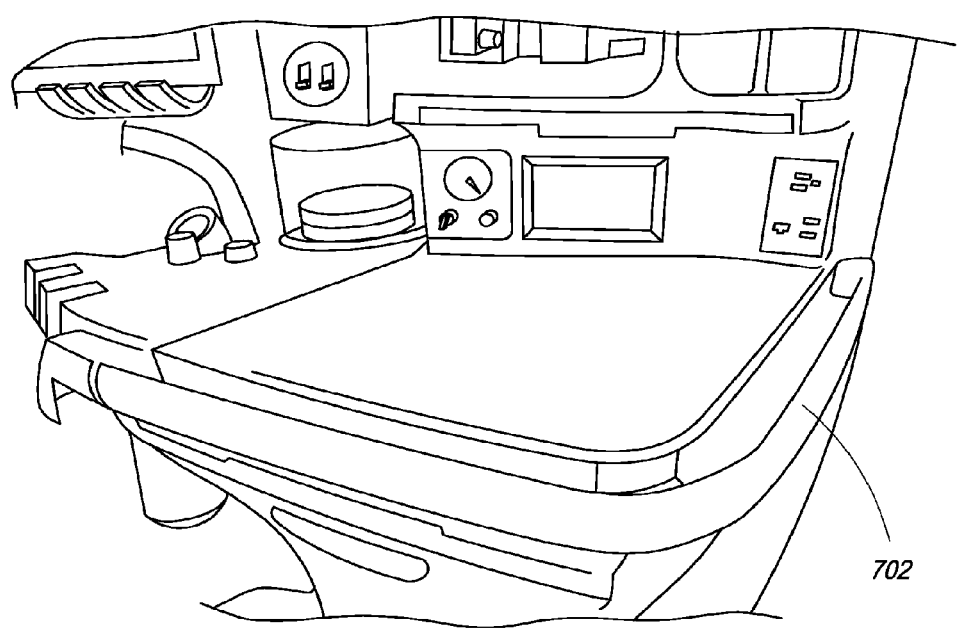
FIG. 7B is an illustration of a handle activated castor lock provided in the AO in accordance with an embodiment of the invention.

FIG. 7A illustrates a handle activated castor lock provided in the AO in accordance with an embodiment of the invention. The handle-based lock 702 allows quick and small adjustments of the position of the anesthesia system. FIG. 7B is a further illustration of handle-based lock 702.

Figure 8:
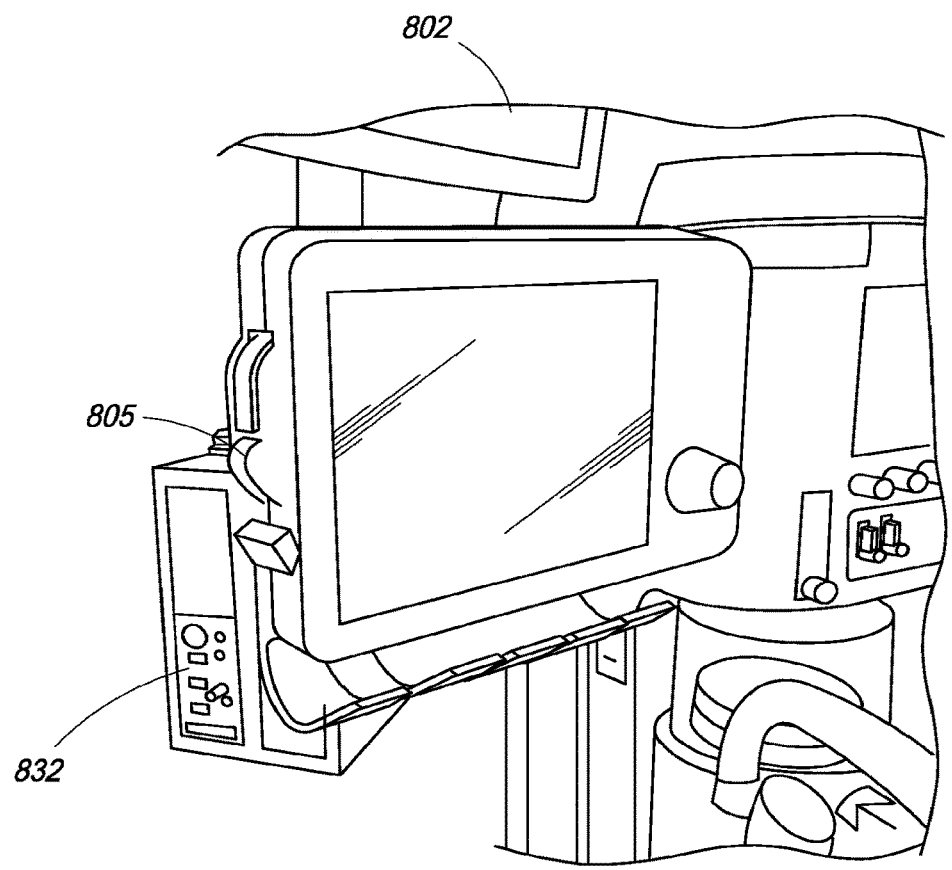
FIG. 8 is an expanded view of a tape dispenser area and physiologic monitor connections provided in the clinical center of the anesthesia system of the present invention.

FIG. 8 illustrates a medical tape dispenser 805 provided on the CC 802 in accordance with an embodiment of the invention. FIG. 8 also shows the physiological monitor (shown as 132 in FIG. 1C) parameter connections 832.

Figure 9A:
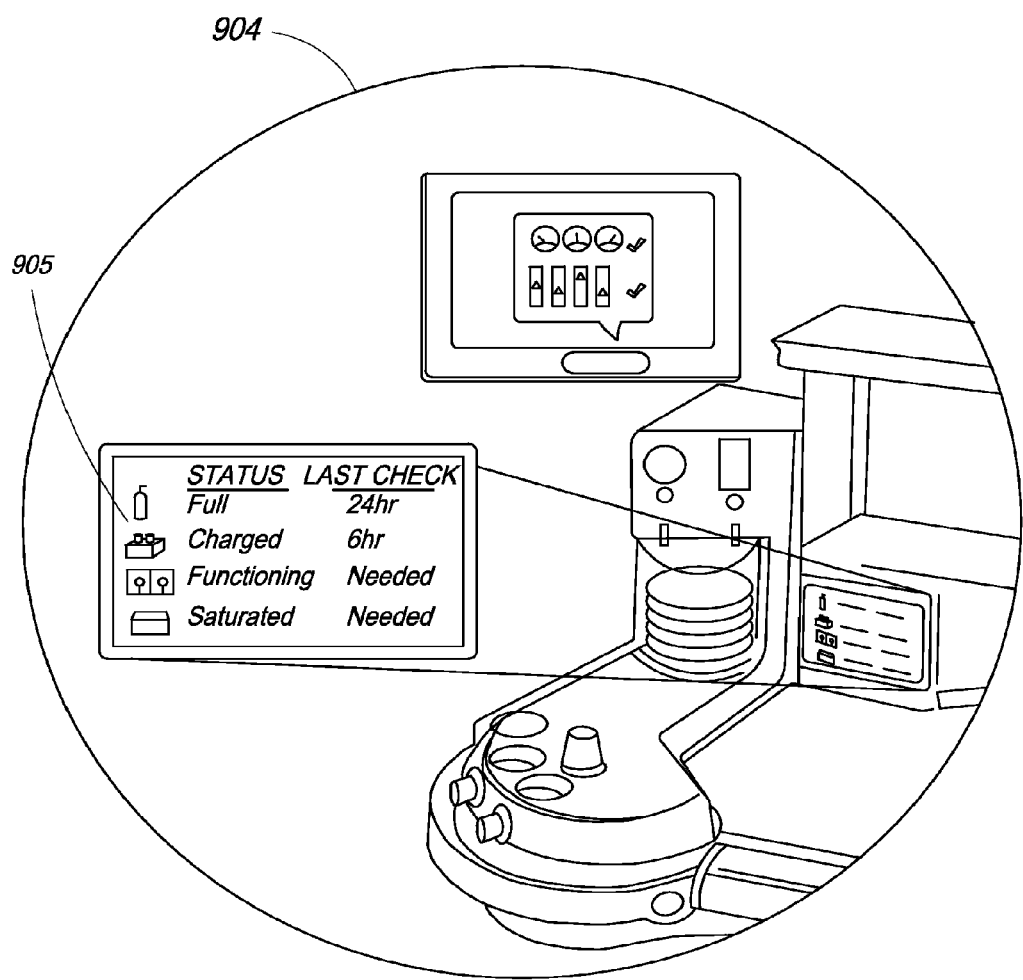
FIG. 9A is a schematic drawing of the system status computer provided with the anesthesia system of the present invention.

As shown in FIG. 9A, in one embodiment, the AO 904 includes a System Status Computer (SSC) 905 for conveying information to the user concerning the status of the anesthesia system's pneumatic, electrical, SW and communication functions. The SSC 905 collects all information related to the technical status of the anesthesia system into one small display unit.

This provides the user with an intuitive separation of the anesthesia system's operation and functional information, from the clinical information associated with the therapy that the system is providing. The SSC 905 off-loads functions from a main clinical display unit (not shown) and provides an intuitive separation of technical measurements from those used directly for clinical care.

In various embodiments the SSC 905 provides information such as: pipeline pneumatic pressures, cylinder pressures, AC electrical power status, DC electrical power status, backup up electrical power (e.g. battery) status, software version, internal CPU serial numbers and revisions, system time and date, timer and alarm status, unit operation hours, last checkout and status, etc. This information can be conveyed either in a numeric format or graphically via fill bars, or emulation of pressure gauges.

Figure 9B:
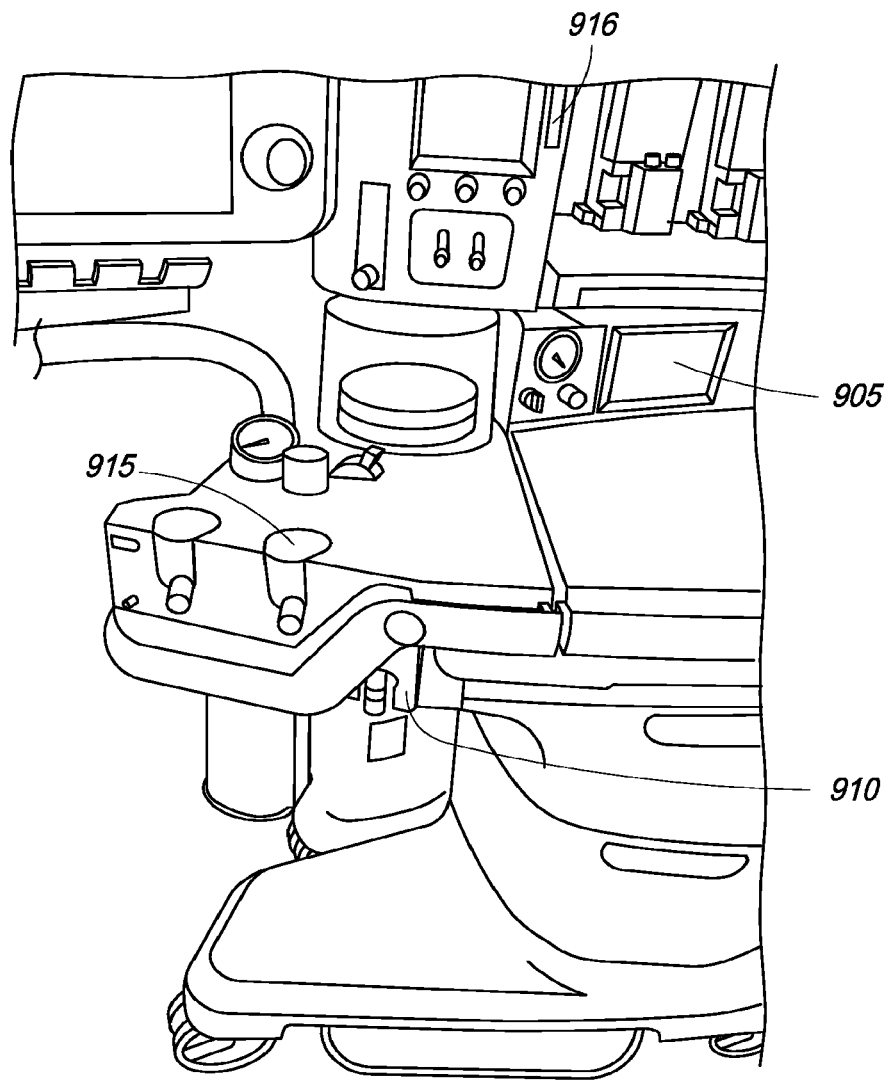
FIG. 9B is an illustration of the information projection lighting feature of the anesthesia system of the present invention.

In one embodiment, the SSC 905 remains powered on, available to present its information, even when the anesthesia system is turned off or disconnected from mains supplies. In this manner, the SSC 905 remains continuously ready to provide all data, but specifically cylinder pressure and pipeline pressure information to the user without activating the main portion of the anesthesia system. The SSC 905 may operate in a sleep/dormant mode when the power of the anesthesia system is turned off in order to conserve power and its display is turned on by a single user touch. The SSC 905 is capable of operating on battery power, allowing observation of system status even if the system is not connected to AC mains. Prior art systems utilize a mix of mechanical gauges and measurements displayed on a clinical display unit in order to convey system status information to the user. In an embodiment, by utilizing flat liquid crystal display (LCD) technology, the SSC 905 can be placed under a transparent surface of the AO, such as a flat work-surface. The collection of all relevant system information in an electronic format obviates the need for mechanical gauges that consume significant space on the usable face of the anesthesia system. In the AO, the space normally used for mechanical gauges in conventional systems, is freed up and is better utilized for storage or other office type functions. FIG. 9B provides an illustration of SSC 905.

Information Projection Lighting

In one embodiment of the present invention, direct lighting of an area of the system in association with an alarm, for example, any area of the anesthesia system being suspected of undergoing a technical problem, is provided, in order to unambiguously and intuitively guide the user's attention to the likely source of the problem reflected by the alarm. Thus, the information projection lighting of the present invention indicates an anomalous operational condition by illuminating the portion of the anesthesia system causing or likely to cause the anomalous/alarm condition.

For example, in an anesthesia system, a case of "sticking" non-return valves (check valves) may manifest as an inability to ventilate a patient. Even though an alarm message indicating a low ventilation condition may be generated, the direct lighting feature of the present invention causes a red flashing light to emanate from the check valve area, thereby guiding the user's attention to the potential source of the problem. In one embodiment, this lighting may be very dispersive in nature causing the whole check valve dome to light with red or other colors. If more than one function of the system could be the cause for the alarm, multiple areas may lighted or a user may be guided to step through them in a sequence, presumably most likely to least likely.

In one embodiment, information projection lighting is used for identification of proper attachments and work zones. For example, many known anesthesia systems use a "Common Gas Outlet" (CGO) for induction purposes. This requires a user to select CGO as the source of common gas using the anesthesia system's controls. To eliminate a potential error of having a patient attached to the CGO without it being selected as the source of the common gas, information projection lighting is used to illuminate the concerned port and attached translucent tube. In one embodiment, as shown in FIG. 9B, if the CGO is not selected, the port 910 is illuminated in a first color, such as amber; if the CGO is selected via rotating the port body to a horizontal position, the port lighting is illuminated in a second color, such as green, while the ports of the circle system 915 are simultaneously illuminated in a third color, such as red, indicating that they are not in use.

Figure 10B:
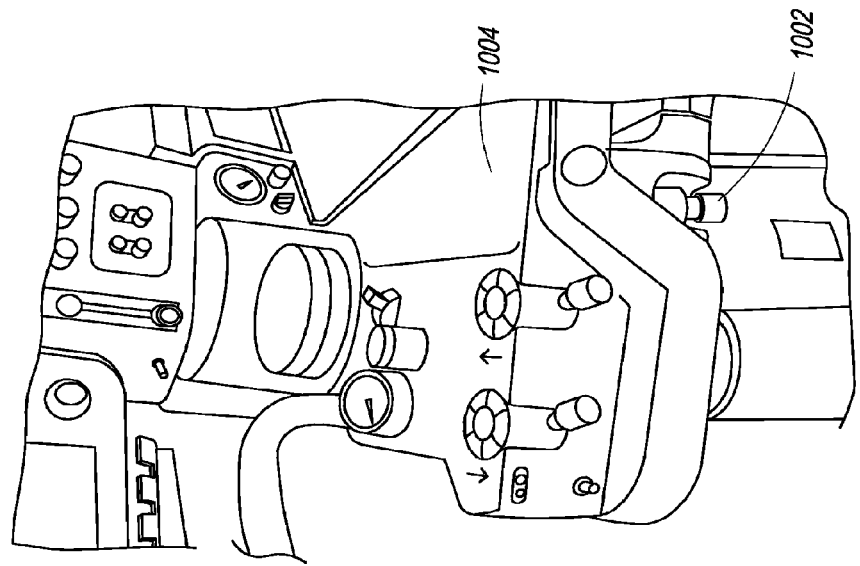
FIG. 10B is an illustration of the CGO gas port provided in the anesthesia system of the present invention, in a vertical and inactive position.
Figure 10A:
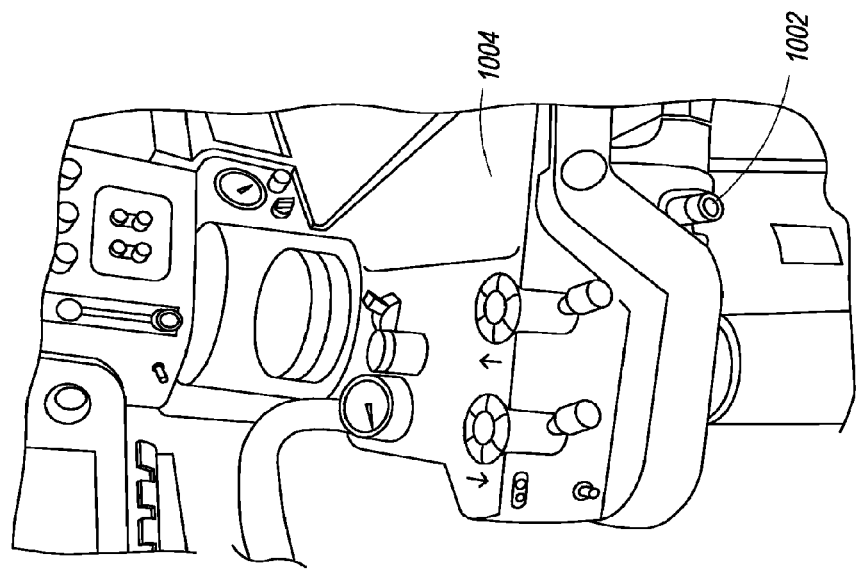
FIG. 10A is an illustration of the CGO gas port provided in the anesthesia system of the present invention, in a horizontal and active position.

Referring now to FIGS. 10A and 10B, a switch 1002 is provided as a two position lever for a moveable CGO that is activated when the port is rotated up to a horizontal position. As shown in FIG. 10A, in a first position, switch 1002 is in a horizontal position and activates the CGO port. The first position is preferably parallel to a work surface 1004 of the system. As shown in FIG. 10B, in a second position, switch 1002 is preferably in a vertical position, and orthogonal to a work surface 1004 of the system and deactivates the movable CGO.

A similar use of the information projection lighting may be made in the bag to vent area. In an embodiment, when "vent" operation is selected, the bellows itself could be lit in any color, such as green. FIGS. 10A and 10B show the bellows 1006 lit when ventilation is active. Similarly, the APL valve and circuit pressure gauge are illuminated with a different light color, such as amber, when the ventilator of the anesthesia system is in an inactive off state.

In one embodiment, information projection lighting is used to indicate status (such as, on/off or engage/disengage or active/inactive) of the plurality of controls by direct illumination of the controlled function. By way of example, with reference to FIG. 1A, the arm of bag 153 is illuminated to indicate ventilator inactive/active or off/on state; the $CO_2$ absorbent canister 155 is illuminated if the canister 155 is disengaged from the breathing circuit and/or if there is an alarm for high $CO_2$ in the respiratory gas; again, the side stream respiratory gas monitor water trap is illuminated if the respiratory gas monitor (housed within physiological monitor 132 of FIG. 1C) is alarming for an obstruction. In various embodiments the information projection lighting may be used for indicating vaporization on/off, circle system ports enabled/disabled depending upon whether the ventilator is in active/inactive state, suction on/off, auxiliary oxygen on/off, carbon dioxide bypass on/off, etc.

Persons of ordinary skill in the art should appreciate that the information projection lighting, of the present invention, is adjustable for color, intensity and/or flashing rate in accordance with a user's needs/preferences.

Hence, the present invention provides a system and method for the identification of problem areas in an anesthesia system in an unambiguous and intuitive manner through the use of subtle lighting of suspected problem areas in association with these alarms. With the present invention, the user will be immediately directed to the area of the system in need of examination or correction and will not incur unnecessary distraction or defocus from patient care. Further, the visual lighting of the affected system area will enable other personnel in the OR to assist in the diagnosis or recognition of the problem. Through information projection visual lighting, operational elements of the system whose function may be engaged or disengaged are clearly identified, decreasing the potential for clinical errors.

Enhanced Flow Tube Visualization

In conventional anesthesia delivery and ventilation systems, flow tubes are commonly used to serve as a simple, clear, and reliable mechanical method to ensure proper operation of a device—often in the event of an electronic failure or as a cross check of the electronic flow readings. As shown in FIG. 9B, the present invention optionally includes an improved visualization method for a flow tube 916 used as a backup to electronic fresh gas flow measurement. An exemplary flow tube is described in U.S. patent application Ser. No. 12/775,719, filed on May 7, 2010 and assigned to the assignee of the present invention, and is herein incorporated by reference in its entirety.

Wireless Proximal Sensor(s)

In an embodiment, the present invention provides a single, small sensor solution for proximal placement without tubes or connections back to the anesthesia system. Using small sensors positioned directly at the airway provides optimal flow and pressure measurement signals. The integral docking station for the wireless sensor not only provides power recharge and signal connection, but also provides a physical storage location for the sensor between cases or when it is not in use. In an embodiment, the anesthesia system of the present invention provides an autoclavable flow sensor with a wireless chipset, including CPU power to perform wireless function, sensor sampling and processing.

In an embodiment, the wireless proximal sensor provides reliable communications in an Operating Room Environment up to a distance of 30 feet. In various embodiments, wireless technologies such as 802.15.4 (low-level IEEE spec for Zigbee), SynkroRF (developed by Freescale), RF4CE (Industry Consortium), ANT and/or ANT+, Bluetooth, Low Power Bluetooth, etc. may be employed. In various embodiments the wireless proximal sensor fits within a battery based power budget and its design is tolerant to high humidity environments.

In one embodiment, an airway pressure sensor having the following characteristics is employed:
Dynamic range: −20 to 120 $cmH_2O$
Resolution: 0.01 $cmH_2O$ (calculates to about 14-bit resolution)
Bandwidth: 60 Hz (Guidance for on board analog and digital filtering)
Output (decimated) sample rate: 250 Hz (4 msec period)

In one embodiment, a differential pressure sensor is employed having the following characteristics:
Dynamic range: ±2.5 $cmH_2O$
Resolution: 0.0004 $cmH_2O$ (Calculates to about 14-bit resolution)
Bandwidth: 60 Hz (Guidance for on board analog and digital filtering)
Output (decimated) sample rate: 250 Hz (4 msec period)

The use of a wireless sensor requires detection of loss of proper signal such as a data dropout for more than 12 to 50 msec, thereby causing the system's internal sensors to be used. Additionally, wireless battery monitoring predicts loss of signal, and a seamless use of backup sensor systems. The anesthesia system of the present invention is provided with this backup means via Fresh Gas Flow sensors and Drive Gas Flow sensor. These sensors form a redundant network of flow information to be used for error checking the proximal sensor and continuity of ventilation delivery if the wireless proximal sensor becomes disabled.

Figure 9C:
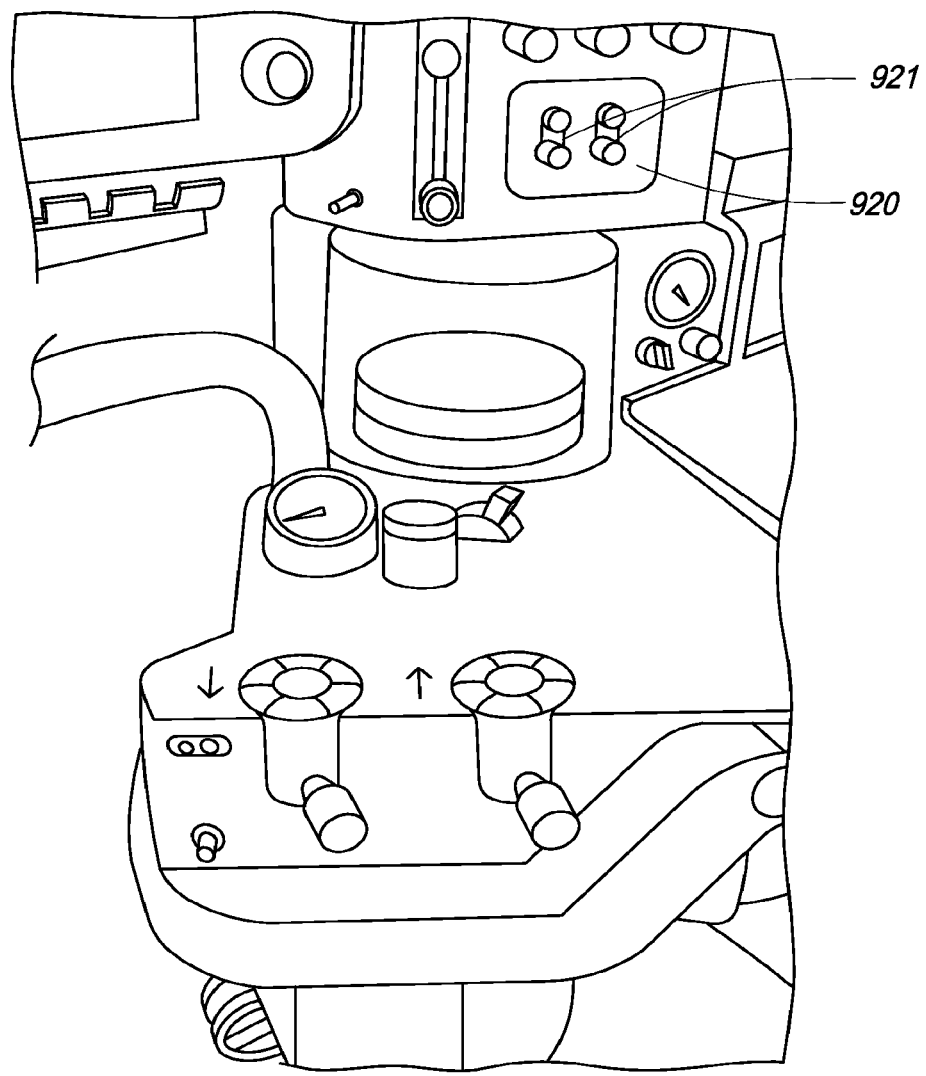
FIG. 9C is an illustration of the wireless sensor and sensor docking feature of the anesthesia system of the present invention.

In an embodiment, as shown in FIG. 9C, an integral "docking" station 920 for the wireless proximal sensors 921 is provided on the anesthesia system that provides a coded data communication channel as well as power for recharging the wireless sensor batteries. The wireless proximal sensor establishes a communication link to the anesthesia system only while physically sitting in the docking station. A user is required to remove the sensor from the docking station 920 and place it at the proximal airway. In an embodiment, the use of lighting as described above in the "Information Projection Lighting" section provides information that the sensor channel is active.

In one embodiment, the wireless sensor is separated into two parts, a wireless communication pod and a sensor pod that is coupled to the wireless communication pod. Only the wireless communication pod, which provides communication to the anesthesia system, is placed into the docking station. For example, the wireless communication "pod" could be attached to a "pitot" type flow sensor, in one embodiment.

Circle-Less Breathing Circuit

In one optional embodiment, the anesthesia system of the present invention provides a circle-less breathing circuit for patients. Most current anesthesia systems employ a 'circle circuit' that contains a $CO_2$ absorbent for recycling some amount of breathing gas which is then conveyed back to the patient. Conventional anesthesia systems also typically employ 'mixers' that combine oxygen, air and nitrogen gases prior to introduction into the circle circuit as 'fresh gas'.

Figure 11A:
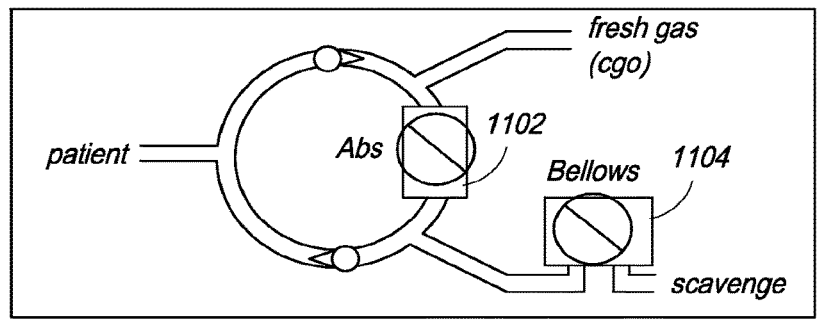
FIG. 11A is a diagram showing some basic elements of a conventional circle breathing circuit indicating which major elements have been eliminated, or are not required, in the circle-less breathing circuit of the anesthesia system of the present invention.

FIG. 11A illustrates some basic elements of a conventional circle breathing circuit indicating which major elements have been eliminated, or are not required, in the circle-less breathing circuit of the present invention. Absorber element 1102 and bellows 1104 have been eliminated in the circle-less breathing circuit provided by the present invention. Further, check valves used in the circuit illustrated in FIG. 11A are also replaced with active valves such as those used in typical, flow valve controlled ICU ventilators.

Figure 11B:
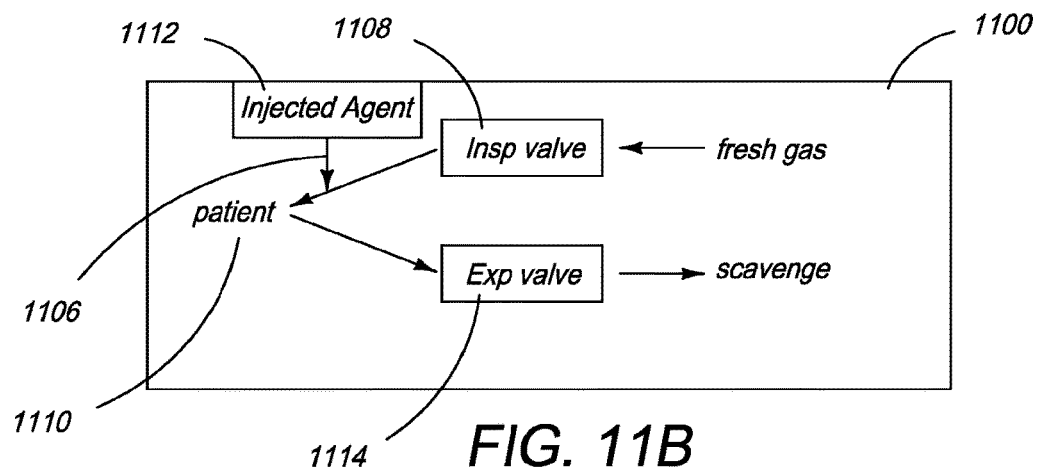
FIG. 11B illustrates a circle-less breathing circuit, in accordance with an embodiment of the anesthesia system of the present invention.

FIG. 11B illustrates a circle-less breathing circuit 1100, in accordance with an embodiment of the present invention. As shown, fresh gas is injected through an inspiratory valve 1108, mixed with an injected agent 1112, delivered to a patient 1110 and then led out via an expiratory valve 1114. In an embodiment, the fresh gas can be oxygen or air, thus requiring only a single control valve for inspiration. In another embodiment, the inspiratory valve 1108 comprises multiple control valves designed to blend oxygen, air and nitrous oxide directly into the circuit. In an embodiment, the source of the fresh gas may be a high pressure pipeline or cylinder supply and the function of the inspiratory valve 1108 may be accomplished with proportional solenoid valves such as those used on conventional ICU ventilators. Alternatively, a low pressure fresh gas source such as room air or oxygen concentrator may be employed and the inspiratory valve 1108 function may be accomplished by employing a turbine or piston device to generate the necessary patient circuit pressures.

In one embodiment the injected agent device 1112 utilizes gaseous anesthetic agent and is designed to control the injection of the agent to just the portions of the gas being delivered to the patient's lungs, since the circle-less circuit does not cause the gas provided through the inspiratory valve to be re-breathed. In an alternate embodiment, the agent is metered as a liquid and is vaporized into the gas stream utilizing a wick arrangement within the inspiratory portion of the breathing circuit tubing 1106.

Using the circle-less breathing circuit 1100, a pulse train of anesthetic gas may be injected in real-time into the inspiratory flow stream of a patient. The goal is to "phase" the pulse train of agent so that a required portion of the pulse lands in the patient's lung and the dead-space receives no agent. In accordance with an embodiment of the present invention, an optional technique to minimize agent usage is to shape the anesthetic gas pulse so that dead-space receives no agent. Typically, dead-space comprises about 20% of the tidal volume. At the end of inspiration, the dead-space is filled with fresh gas; "phasing" the pulse train of the agent can help ensure that this trailing gas contains no anesthetic agent.

Figure 11C:
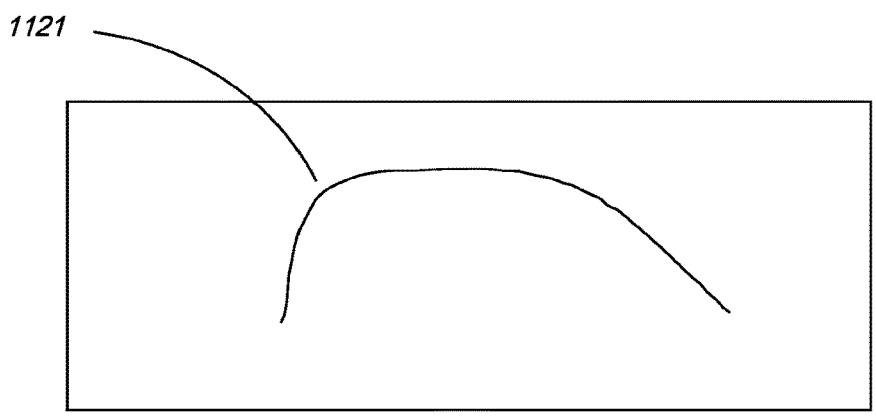
FIG. 11C illustrates an optimally shaped anesthetic gas pulse so that a pulse train of anesthetic gas may be injected in real-time into the inspiratory flow stream of a patient.

Also, since the patient is lying down, most of the posterior portion of the lung is perfused while the anterior portion is relatively less perfused. Hence, an optimal shape of the pulse 1121 is square with some taper towards the end, as illustrated in FIG. 11C. In an embodiment, a gas monitor is employed to help with the dead-space and pulse phasing. Thus, the $VCO_2$ (volume of patient-generated carbon dioxide) and $EtCO_2$ (end-tidal carbon dioxide) can be used to determine the dead-space which is about equal to the volume of the endotracheal tube (ETT).

The agent injection is then linked to the delivery of an inspiration breath and the end of agent delivery is phased to the inspiratory gas volume that is projected to enter the dead space.

Hence, the anesthesia system of the present invention provides a circle-less breathing system at a lower cost than conventional circular breathing circuits as a plurality of elements of conventional circuit such as bellows, absorber, replaceable absorber canister, mixer and conventional vaporizer, etc. have been eliminated. Further, by using the present circle-less breathing circuit 1100, soda lime (or substitutes) are removed from the environmental waste streams, and drive gas (or other form of energy) is not necessarily required, thereby making the use of an oscillating pump for air and an oxygen concentrator as less power is required to run the circuit. Since, in the present circuit, the inspired gas is always clean, the circuit is optimal as far as infection control is concerned and is also easier to maintain, resulting in a lower cost of ownership. Further, it has been observed that clinicians are frequently confused regarding the dilution effects of the circle circuit, thereby resorting to Inspired Gas Control (IGC) or Expired Gas Control (EGC) systems. The present circle-less breathing circuit 1100 provides IGC automatically, since there is no dilution effect. In an embodiment, the inspiratory valve feature may be implemented entirely in software and flows much higher than a traditional mixer may be achieved.

Electronic Vaporization

Contemporary anesthetic vaporizer systems contain valves and/or wick systems for transitioning liquid anesthetic agent into a gaseous form. Typically, these systems provide an agent concentration level of 0-10% (although sometimes higher for Suprane) of the gas being used as "fresh gas" or "make-up" gas in a circle breathing system. Contemporary devices are rather complex and require precision mechanical components or flow control systems to operate, creating a relatively high cost device. A new type of vaporizer element has been described in U.S. Pat. No. 6,155,255 that utilizes direct liquid injection into a low cost "wick" arrangement. This device is extremely simple, but would need to be integrated into a system where the flow by the wick is known in order to be practical. Further, the design of the liquid injection system would be critical for proper functioning and would not be optimized by use of a standard syringe pump as described in U.S. Pat. No. 6,155,255.

The present invention provides a method by which vaporizer elements, such as the one described in U.S. Pat. No. 6,155,255, may be integrated into an anesthesia system, for practical use as an electronic vaporizer. In an embodiment, a micro-piezo pump is used for pumping the liquid to be vaporized. Injection of the liquid is measured in a supply line supplying liquid to the vaporizer, and control is accomplished using a feedback loop. Measurement of liquid flow into the evaporator (i.e. wick) and measurement of gas flow either into or out of the evaporator (difference being anesthetic vapor) is used in order to determine concentration of anesthetic agent. This step is performed alternative to or in conjunction with anesthetic agent concentration measurement at the patient site. Further, pulsing (i.e. increasing or decreasing) of liquid flow in conjunction with gas flow changes through the evaporator may be performed. The evaporator is placed in the main flow stream of a circle-less breathing circuit anesthesia system, such as the one described in the preceding section. A control unit controlling the liquid flow into the evaporator is connected to the display of an anesthesia system, integrating the vaporizer subsystem as a component of a broader anesthesia system of the present invention. This allows agent data to be presented with fresh gas flow rates and patient tidal volumes.

In one embodiment a valve is added to a known electronic vaporizer, such as the one described in U.S. Pat. No. 6,155,255, and is controlled to provide for an immediate gas flow bypass of the evaporator. This is used for an oxygen flush of the system or for immediately turning off of the vaporizer. Proportional control of this bypass may also be used to quickly reduce the amount of vapor being added without entirely ceasing the vapor addition, as is the case with a complete bypass. Further, a component of the fresh gas flow (e.g. Oxygen) may be selectively passed through the evaporator in order to obtain a consistent uptake of anesthetic agent vapor. In an embodiment, a liquid type agent detection means is added to either a pump connected to an external container of the liquid anesthetic (from which the liquid anesthetic is pumped into the vaporizer) or the container itself for determining the anesthetic type. Further the container may comprise a plurality of reservoirs, the operation of each controlled by a pump controller unit, thereby allowing for multiple anesthetic agent types to be present on a single anesthesia machine. The reservoir(s) containing the anesthetic agents may be cooled to maintain anesthetic agents in liquid form for injection by the liquid injection means of a pump—connected to pump the agents into the vaporizer. In various embodiments various protection means and means for elimination of liquid cavitation are employed. Examples of such means comprise cooling of one or more pumps to prevent cavitation as the anesthetic liquid is pumped through, pressurizing of anesthetic agent reservoirs into a connected pump to prevent cavitation, employing cavitation detection means in the pump or a supply line connecting the reservoirs to the pump, employing specific known design features in the supply line or pump to prevent cavitation, and adding resistance to the supply line thereby creating backpressure in order to prevent cavitation.

The method of the present invention allows for selection of different evaporator sizes based on the amount of fresh gas flow. For example, an anesthesia control means (such as a knob or switch) could select either a high flow or a low flow evaporator depending on the amount of fresh gas flow being used. Also, an On/Off valve may be employed in the anesthetic agent supply line as a safety control to immediately stop liquid injection into the evaporator. In an embodiment, a sensor element is positioned at the patient airway for reading the optical absorption of the gas being inspired by the patient at different light wavelengths, and the signals sensed at that point are used for performing either inspired gas control or expired gas control using the vaporizer as a subsystem of an anesthesia machine. Further, in an embodiment, two liquid flow sensors are used in series, one high flow and one for lower flow, in order to sense the full range of liquid flow rates at sufficient accuracy.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An anesthesia delivery system, comprising:
a first section comprising support for at least one clinical control and at least one patient connection for providing therapy to a patient, wherein said at least one patient connection includes a breathing circuit connection comprising at least one limb, wherein the at least one limb may be inspiratory, expiratory or a combination thereof;
a second section, comprising a base portion for supporting and housing the first section and at least one pneumatic or electrical connection, wherein the first section is linearly, rotatably or linearly and rotatably extendable relative to the second section, and wherein the second section is pneumatically connected to the first section via a suction supply line or an anesthesia gas supply line; and
a lighting system for indicating a status of at least one function of the anesthesia delivery system by direct illumination.

2. The anesthesia delivery system of claim 1 further comprising adjustable lighting, wherein the adjustable lighting is configured to be adjusted by color, intensity or flash rate.

3. The anesthesia delivery system of claim 1 wherein the lighting system is configured to indicate an anomalous operational condition of the anesthesia delivery system by direct illumination of a portion of the anesthesia delivery system suspected of causing the anomalous operating condition.

4. The anesthesia delivery system of claim 1 wherein the lighting system is configured to indicate when a ventilator within the anesthesia delivery system is in an active state by illuminating a bellows of the ventilator.

5. The anesthesia delivery system of claim 1 wherein the lighting system is configured to indicate when a ventilator within the anesthesia delivery system is in an inactive state by illuminating an APL valve of the ventilator.

6. The anesthesia delivery system of claim 1 wherein the lighting system is configured to indicate when a ventilator within the anesthesia delivery system is in an inactive state by illuminating a pressure gauge of the ventilator.

7. The anesthesia delivery system of claim 1 wherein the lighting system is configured to indicate when a ventilator within the anesthesia delivery system is in an inactive state by illuminating a bag arm of the ventilator.

8. The anesthesia delivery system of claim 1 wherein the lighting system is configured to illuminate a common gas outlet port of the anesthesia delivery system when controls are set to have gas emerge from the common gas outlet port.

9. The anesthesia delivery system of claim 1 wherein the lighting system is configured to illuminate an auxiliary flow tube if auxiliary flow has been turned on.

10. The anesthesia delivery system of claim 1 wherein the lighting system is configured to illuminate a $CO_2$ absorbent canister indicating a $CO_2$ level status when the $CO_2$ absorbent canister is not present in a breathing circuit and/or when there is an alarm for high $CO_2$ levels in respiratory gas.

11. The anesthesia delivery system of claim 1 wherein the lighting system is configured to illuminate a side stream respiratory gas monitor water trap if a respiratory gas monitor is alarming to indicate an obstruction.

12. An anesthesia system for delivering a predetermined continuous supply of one or more medical gases mixed with a predetermined concentration of an anesthetic vapor to a patient and for monitoring at least a pressure and a flow rate of the delivered medical gases comprising
a lighting system for indicating an operational status of at least one predefined portion of the anesthesia system wherein the lighting system is configured to illuminate the at least one predefined portion of said anesthesia system based upon an operational status of the at least one predefined portion wherein the operational status comprises at least one of on/off, active/inactive, or anomalous operation states and wherein said predefined portion comprises at least one of a bellows, an adjustable pressure-limiting (APL) valve, a pressure gauge, an auxiliary flow control port, or a bag arm.

13. The anesthesia system of claim 12, wherein said lighting system is configured to illuminate a common gas outlet port (CGO) of said anesthesia system when one or more controls are set to allow at least one gas to emerge from said CGO port.

14. The anesthesia system of claim 12, wherein said lighting system is configured to illuminate a common gas outlet port (CGO) of the anesthesia system in a first color if said CGO port is not selected and is in a first vertical, downward facing position, and in a second color when said CGO port is selected via rotating a body of said CGO port from said first vertical, downward facing position to a second horizontal, forward facing position.

15. The anesthesia system of claim 12, wherein the lighting system is configured to illuminate an inspiratory and an expiratory port of the anesthesia system when one or more controls are set to inhibit gas from emerging from a common gas outlet (CGO) port of said anesthesia system.

16. The anesthesia system of claim 12, wherein said lighting system is configured to illuminate a carbon dioxide absorbent canister of said anesthesia system indicating a $CO_2$ level status when the carbon dioxide absorbent canister is not present in a breathing circuit of said anesthesia system and/or when a level of carbon dioxide gas indicated in a respiratory gas monitor of said anesthesia system rises above a predetermined level.

17. The anesthesia system of claim 12, wherein said lighting system is configured to illuminate a side stream respiratory gas monitor water trap control of said anesthesia system when there is an obstruction in said side stream respiratory gas monitor water trap control.

18. The anesthesia system of claim 12, wherein said lighting system is configured to illuminate multiple portions of said anesthesia system when more than one portion is suspected of causing an anomalous operational state, wherein illumination from the lighting system is configured to vary in at least one of color, flashing rate, pattern, or intensity for guiding a user to inspect illuminated portions in a particular sequence.

19. The anesthesia system of claim 12, wherein the lighting system is configured to illuminate based on a particular lighting pattern and with specific characteristics, wherein said characteristics comprise any one or more of color, flashing rate, and intensity.

20. The anesthesia system of claim 19, wherein said characteristics are user adjustable.

* * * * *